US007723069B2

(12) United States Patent
Soll et al.

(10) Patent No.: US 7,723,069 B2
(45) Date of Patent: May 25, 2010

(54) SITE SPECIFIC INCORPORATION OF PHOSPHOSERINE INTO POLYPEPTIDES USING PHOSPHOSERYL-TRNA SYNTHETASE

(75) Inventors: Dieter Soll, Hamden, CT (US); Jesse Rinehart, New Haven, CT (US)

(73) Assignee: Yale University, New Haven, CT (US)

( * ) Notice: Subject to any disclaimer, the term of this patent is extended or adjusted under 35 U.S.C. 154(b) by 903 days.

(21) Appl. No.: 11/396,439

(22) Filed: Apr. 3, 2006

(65) Prior Publication Data

US 2007/0077620 A1 Apr. 5, 2007

Related U.S. Application Data

(60) Provisional application No. 60/668,726, filed on Apr. 5, 2005.

(51) Int. Cl.
*C12P 21/06* (2006.01)
*C07H 21/00* (2006.01)

(52) U.S. Cl. ..................... 435/69.1; 536/23.1
(58) Field of Classification Search ............. None
See application file for complete search history.

(56) References Cited

U.S. PATENT DOCUMENTS 6,503,729 B1 * 1/2003 Bult et al. ............. 435/69.1
2003/0082575 A1 5/2003 Schultz et al.

OTHER PUBLICATIONS

Altschul et al., "Basic local alignment search tool", *J. Mol. Biol.*, 215(3):403-410 (1990).
Ambrogelly, et al., "Cys-tRNACys formation and cysteine biosynthesis in methanogenic archaea: two faces of the same problem?", *Cell. Mol. LifeSci.*, 61:2437-45 (2004).
Arslan, et al., "Structurally modified firefly luciferase. Effects of amino acid substitution at position 286", *Journal of the American Chemical Society*, 119(45):10877-10887 (1997).
Balch, et al., "Transport of coenzyme M (2-mercaptoethanesulfonic acid) in *Methanobacterium ruminantium*", *J. Bacteriol*, 137:264 (1979).
Basurko, et al., Phosphoserine aminotransferase, the second step-catalyzing enzyme for serine biosynthesis', *IUBMB Life*, 48:525-9 (1999).
Bentin, et al., "Photoreactive bicyclic amino acids as substrates for mutant *Escherichia coli* phenylalanyl-tRNA synthetases", *J. Biol. Chem.* 279:19839-45 (2004).
Bilokapic, et al., "The unusual methanogenic seryl-tRNA synthetase recognizes tRNASer species from all three kingdoms of life", *Eur. Journ. Biochemistry*, 271(4):694-702 (2004).
Blight, et al., "Direct charging of tRNA(CUA) with pyrrolysine in vitro and in vivo", *Nature*, 431(7006):333-5 (2004).
Buchner, et al., "A method for increasing the yield of properly folded recombinant fusion proteins: single-chain immunotoxins from renaturation of bacterial inclusion bodies", *Anal. Biochem.*, 205: 263-270 (1992).

Calendar and Berg, "Purification and physical characterization of tyrosyl ribonucleic acid synthetases from *Escherichia coli* and *Bacillus subtilis*", *Biochemistry*, 5(5):1681-90 (1966).
Calendar and Berg, "The catalytic properties of tyrosyl ribonucleic acid synthetases from *Escherichia coli* and *Bacillus subtilis*", *Biochemistry*, 5(5):1690-5 (1966).
Chatterji and Pachter, "Large multiple organism gene finding by collapsed Gibbs sampling", *J Comput Biol.*, 12(6):599-608 (2005).
Daly and Hearn, "Expression of heterologous proteins in *Pichia pastoris*: a useful experimental tool in protein engineering and production", *J. Mol. Recognit.*, 18(2):119-38 (2005).
Das and Vothknecht, "Phenylalanyl-tRNA synthetase from the archaeon Methanobacterium thermoautotrophicum is an (alphabeta)2 heterotetrameric protein", *Biochimie*, 81(11):1037-9 (1999).
Debinski, et al., "A wide range of human cancers express interleukin 4 (IL4) receptors that can be targeted with chimeric toxin composed of IL4 and *Pseudomonas exotoxin*", *J. Biol. Chem.*, 268: 14065-14070 (1993).
Ellman, et al., "Biosynthetic method for introducing unnatural amino acids site-specifically into proteins", *Methods Enzymol.*, 202:301-36 (1991).
Engelhard, et al., "The insect tracheal system: a conduit for the systemic spread of *Autographa californica* M nuclear polyhedrosis virus", *Proc. Natl. Acad. Sci. USA*, 91:3224-3227 (1994).
Fabrega, et al., "An aminoacyl tRNA synthetase whose sequence fits into neither of the two known classes", *Nature*, 411:110-4 (2001).
Fleer, et al., "High-level secretion of correctly processed recombinant human interleukin-1 beta in *Kluyveromyces lactis*", *Gene*, 107:285-95 (1991).
Florens, et al., A proteomic view of the *Plasmodium falciparum* life cycle *Nature*, 419, 520-6 (2002).
Fromm, et al., "Expression of genes transferred into monocot and dicot plant cells by electroporation" *Proc. Natl. Acad. Sci. USA*, 82, 5824-8 (1985).
Giometti, et al., "Global analysis of a "simple" proteome: *Methanococcus jannaschii*", *J. Chromatogr. B Anal. Technol. Biomed. Life Sci.*, 782(1-2):227-43 (2002).
Harrington, et al., "Formation of de novo centromeres and construction of first-generation human artificial microchromosomes", *Nat Genet.*, 15:345-355 (1997).
Hitzeman, et al., "Isolation and characterization of the yeast 3-phosphoglycerokinase gene (PGK) by an immunological screening technique", *J. Biol. Chem.*, 255:12073-80 (1980).

(Continued)

*Primary Examiner*—Eileen B O Hara
(74) *Attorney, Agent, or Firm*—Pabst Patent Group LLP

(57) ABSTRACT

Nucleic acids encoding genes with SepRS and tRNASep activity for site specific incorporation of phosphoserine into a protein or polypeptide and methods of use thereof are described. Typically, SepRS preferentially aminoacylates tRNASep with O-phosphoserine and the tRNASep recognizes at least one codon such as a stop codon. In a preferred embodiment the nucleic acids are on vectors. In one embodiment, the vectors are expressed in cells such as bacterial cells, archeaebacterial cells, and eukaryotic cells. In an alternative embodiment, the vectors are expressed in an in vitro transcription/translation system. Proteins or polypeptides containing phosphoserine produced by the methods described herein can be used for a variety of applications such as research, antibody production, protein array manufacture and development of cell-based screens for new drug discovery.

15 Claims, 3 Drawing Sheets

OTHER PUBLICATIONS

Hohsaka, et al., "Five-base codons for incorporation of nonnatural amino acids into proteins", *Nucleic Acids Res.*, 29:3646-3651 (2001).
Holland and Holland, "Isolation and identification of yeast messenger ribonucleic acids coding for enolase, glyceraldehyde-3-phosphate dehydrogenase, and phosphoglycerate kinase", *Biochem.*, 17:4900-7 (1978).
IBBA, et al., "The adaptor hypothesis revisited", *Trends Biochem. Sci.*, 25:311-6 (2000).
Jansen, et al., "Drag&Drop cloning in yeast", *Gene*, 344:43-51 (2005).
Karlin and Altschul, "Applications and statistics for multiple high-scoring segments in molecular sequences", *Proc. Nat'l. Acad. Sci. USA*, 90:5873-5787 (1993).
Kim, et al., "Sequence Divergence of Seryl-tRNA Synthetases in Archaea", *J. Bacteriol.*, 180:6446-49 (1998).
Klein, et al., "High velocity microprojectiles for delivering nucleic acids into living cells", *Nature*, 327:70-73 (1987).
Kreitman and Pastan, "Purification and characterization of IL6-PE4E, a recombinant fusion of interleukin 6 with *Pseudomonas exotoxin*", *Bioconjug. Chem.*, 4:581-585 (1993).
Li, et al., "Cysteinyl-tRNA formation: the last puzzle of aminoacyl-tRNA synthesis", *FEBS Lett.*, 462:302 (1999).
Li, et al., "Usage of an intronic promoter for stable gene expression in *Saccharomyces cerevisiae,*", *Lett Appl Microbiol.*, 40(5):347-52 (2005).
Lipman, et al., "Synthesis of cysteinyl-tRNA(Cys) by a genome that lacks the normal cysteine-tRNA synthetase" *Biochemistry* 39:7792-8 (2000).
Logan and Shenk, "Adenovirus tripartite leader sequence enhances translation of mRNAs late after infection" *Proc. Natl. Acad. Sci. USA*, 81:3655-3659 (1984).
Maccoss, et al., "Probability-based validation of protein identifications using a modified SEQUEST algorithm", *Anal. Chem.*, 74:5593-9 (2002).
Margelevicius and Venclovas, "PSI-BLAST-ISS: an intermediate sequence search tool for estimation of the position-specific alignment reliability", *BMC Bioinformatics*, 6:185 (2005).
Min, et al., "Transfer RNA-dependent amino acid biosynthesis: an essential route to asparagine formation", *Proc. Natl. Acad. Sci. U.S. A.*, 99:2678 (2002).
Mino and Ishikawa, "A novel O-phospho-L-serine sulfhydrylation reaction catalyzed by O-acetylserine sulfhydrylase from *Aeropyrum pernix* K1", *FEBS Lett.*, 551:133-8 (2003).
Mizutani, et al., "Possible incorporation of phosphoserine into globin readthrough protein via bovine opal suppressor phosphoseryl-tRNA", *FEBS Lett.*, 207(1):162-6 (1986).
Moore, "On the Determination of Cystine as Cysteic Acid", *J. Biol. Chem.*, 238:235-7 (1963).
Needleman and Wunsch, "A general method applicable to the search for similarities in the amino acid sequence of two proteins", *J. Mol. Biol.*, 4(3):443-53 (1970).
Pearson and Lipman, "Improved tools for biological sequence comparison", *Proc. Nat'l. Acad. Sci. USA*, 85:2444-8 (1988).

Polycarpo, et al., "Activation of the pyrrolysine suppressor tRNA requires formation of a ternary complex with class I and class II lysyl-tRNA synthetases", *Mol.Cell*, 12:287-94 (2003).
Polycarpo, et al., "An aminoacyl-tRNA synthetase that specifically activates pyrrolysine", *Proc. Natl. Acad. Sci. U.S.A.*, 101;12450 (2004).
Rothman, et al., "Caged phosphoproteins", *Journal of the American Chemical Society*, 127(3):846-7 (2005).
Ruan, et al., "Cysteinyl-tRNA(Cys) formation in *Methanocaldococcus jannaschii*: the mechanism is still unknown", *J. Bacteriol.* 186, 8-14 (2004).
Sadygov and Yates, A hypergeometric probability model for protein identification and validation using tandem mass spectral data and protein sequence databases', *Anal. Chem.*, 75:3792-8 (2003).
Sandig, et al., "Gene transfer into hepatocytes and human liver tissue by baculovirus vectors", *Hum. Gene Ther.*, 7:1937-1945 (1996).
Smith and Waterman, "Comparison of Biosequences", *Adv. Appl. Math.*, 2:482-89 (1981).
Stathopoulos, et al., "Cysteinyl-tRNA synthetase is not essential for viability of the archaeon *Methanococcus maripaludis*", *Proc. Natl. Acad. Sci. U.S.A.*, 98:14292-7 (2001).
Stathopoulos, et al., "One polypeptide with two aminoacyl-tRNA synthetase activities", *Science*, 287(5452):479-82 (2000).
Tabb, et al., "DTASelect and Contrast: tools for assembling and comparing protein identifications from shotgun proteomics", *J. Proteome Res.*, 1:21-6 (2002).
Takamatsu, et al., "Expression of bacterial chloramphenicol acetyltransferase gene in tobacco plants mediated by TMV-RNA", *EMBO J.*, 6:307-311 (1987).
Tomari, et al., "The role of tightly bound ATP in *Escherichia coli* tRNA nucleotidyltransferase", *Genes Cells*, 5:68998 (2000).
Tumbula, et al., "Transformation of *Methanococcus maripaludis* and identification of a *Pst*I-like restriction system", *FEMS Microbial. Lett.*, 121:309-14(1994).
Van Heeke and Schuster, "Expression of human asparagine synthetase in *Escherichia coli*", *J. Biol. Chem.*, 264:5503-5509 (1989).
Varshney, et al., "Direct analysis of aminoacylation levels of tRNAs in vivo. Application to studying recognition of *Escherichia coli* initiator tRNA mutants by glutaminyl-tRNA synthetase", *J. Biol. Chem.* 266:24712 (1991).
White, "The biosynthesis of cysteine and homocysteine in *Methanococcus jannaschii*", *Biochim. Biophys. Acta*, 1624:46-53 (2003).
Whitman, et al., "Isolation and characterization of 22 mesophillic methanococci", *Syst. Appl. Microbiol.* 7:235-40 (1986).
Wolfson and Uhlenbeck, "Modulation of tRNAAla identity by inorganic pyrophosphatase", *Proc. Natl. Acad. Sci. U.S.A.*, 99:5965-70 (2002).
Zhang and Hou, "Synthesis of cysteinyl-tRNACys by a prolyl-tRNA synthetase", *RNA Biol.*, 1:35-41 (2004).
Zhu, et al., Shotgun Proteomics of *Methanococcus jannaschii* and insights into methanogenesis', *J. Proteome Res.*, 3:538 (2004).

* cited by examiner

SEQUENCE LISTING

<160> NUMBER OF SEQ ID NOS: 13

<210> SEQ ID NO 1
<211> LENGTH: 72
<212> TYPE: DNA
<213> ORGANISM: Methanocaldococcus jannaschii

<400> SEQUENCE: 1

```
gccggggtag tctaggggct aggcagcgga ctgcagatcc gccttacgtg ggttcaaatc      60
ccacccccgg ct                                                          72
```

<210> SEQ ID NO 2
<211> LENGTH: 1650
<212> TYPE: DNA
<213> ORGANISM: Methanocaldococcus jannaschii

<400> SEQUENCE: 2

```
atgaaattaa aacataaaag ggatgataaa atgagatttg atataaaaaa ggttttagag      60
ttagcagaga aggattttga dacggcatgg agagagacaa gggcattaat aaaggataaa     120
catattgaca ataaatatcc aagattaaag cctgtctatg gaaagccaca tccagtgatg     180
gagacgatag agagattaag acaagcttat ctaagaatgg gatttgaaga gatgattaat     240
ccagttatcg ttgatgagat ggagatttat aagcaatttg gaccagaagc aatggcagtt     300
ttagatagat gttttacctt ggctggatta ccaaggccag atgttggttt aggaaatgag     360
aaggttgaga ttataaaaaa tttgggcata gatatagatg aggagaaaaa agagaggttg     420
agagaagttt tacatttata caaaaaagga gctatagatg gggatgattt agtctttgag     480
attgccaaag ctttaaatgt gagtaatgaa atgggattga aggttttaga aactgcattt     540
cctgaattta aagatttgaa gccagaatca acaactctaa ctttaagaag ccacatgaca     600
tctgggtggt ttataactct aagcagttta ataagaagaa gaaaactgcc tttaaagtta     660
ttctctatag atagatgttt tagaagggag caaagagagg atagaagcca tttaatgagt     720
tatcactctg catcttgtgt agttgttggt gaagatgtta gtgtagatga tggaaaggta     780
gttgctgaag gattgttggc tcaatttgga tttacaaaat ttaagtttaa gccagatgag     840
aaaaagagta agtattatac accagaaact caaacagagg tttatgccta tcatccaaag     900
ttgggagagt ggattgaagt agcaaccttt ggagtttatt caccaattgc attagctaaa     960
tataacatag atgtgccagt tatgaacctt ggcttaggag ttgagaggtt ggcaatgatt    1020
atttacggct atgaggatgt tagggcaatg gtttatcctc aattttatga atacaggttg    1080
agtgatagag atatagctgg gatgataaga gttgataaag ttcctatatt ggatgaattc    1140
tacaactttg caaatgagct tattgatata tgcatagcaa ataaagataa ggaaagccca    1200
tgttcagttg aagttaaaag ggaattcaat ttcaatgggg agagaagagt aattaaagta    1260
```

-continued

```
gaaatatttg agaatgaacc aaataaaaag cttttaggtc cttctgtgtt aaatgaggtt    1320
tatgtctatg atggaaatat atatggcatt ccgccaacgt ttgaagggt taaagaacag    1380 tatatcccaa ttttaaagaa agctaaggaa gaaggagttt ctacaaacat tagatacata   1440
gatgggatta tctataaatt agtagctaag attgaagagg ctttagtttc aaatgtggat   1500
gaatttaagt tcagagtccc aatagttaga agtttgagtg acataaacct aaaaattgat   1560
gaattggctt taaaacagat aatggggag aataaggtta tagatgttag gggaccagtt    1620
ttcttaaatg caaaggttga gataaaatag                                    1650
```

<210> SEQ ID NO 3
<211> LENGTH: 549
<212> TYPE: PRT
<213> ORGANISM: Methanocaldococcus jannaschii

<400> SEQUENCE: 3

```
Met Lys Leu Lys His Lys Arg Asp Asp Lys Met Arg Phe Asp Ile Lys
1               5                   10                  15

Lys Val Leu Glu Leu Ala Glu Lys Asp Phe Glu Thr Ala Trp Arg Glu
            20                  25                  30

Thr Arg Ala Leu Ile Lys Asp Lys His Ile Asp Asn Lys Tyr Pro Arg
        35                  40                  45

Leu Lys Pro Val Tyr Gly Lys Pro His Pro Val Met Glu Thr Ile Glu
    50                  55                  60

Arg Leu Arg Gln Ala Tyr Leu Arg Met Gly Phe Glu Glu Met Ile Asn
65                  70                  75                  80

Pro Val Ile Val Asp Glu Met Glu Ile Tyr Lys Gln Phe Gly Pro Glu
                85                  90                  95

Ala Met Ala Val Leu Asp Arg Cys Phe Tyr Leu Ala Gly Leu Pro Arg
            100                 105                 110

Pro Asp Val Gly Leu Gly Asn Glu Lys Val Glu Ile Ile Lys Asn Leu
        115                 120                 125

Gly Ile Asp Ile Asp Glu Glu Lys Lys Glu Arg Leu Arg Glu Val Leu
    130                 135                 140

His Leu Tyr Lys Lys Gly Ala Ile Asp Gly Asp Asp Leu Val Phe Glu
145                 150                 155                 160

Ile Ala Lys Ala Leu Asn Val Ser Asn Glu Met Gly Leu Lys Val Leu
                165                 170                 175

Glu Thr Ala Phe Pro Gly Phe Lys Asp Leu Lys Pro Glu Ser Thr Thr
            180                 185                 190

Leu Thr Leu Arg Ser His Met Thr Ser Gly Trp Phe Ile Thr Leu Ser
        195                 200                 205

Ser Leu Ile Lys Lys Arg Lys Leu Pro Leu Lys Leu Phe Ser Ile Asp
    210                 215                 220

Arg Cys Phe Arg Arg Glu Gln Arg Glu Asp Arg Ser His Leu Met Ser
225                 230                 235                 240

Tyr His Ser Ala Ser Cys Val Val Val Gly Glu Asp Val Ser Val Asp
                245                 250                 255

Asp Gly Lys Val Val Ala Glu Gly Leu Leu Ala Gln Phe Gly Phe Thr
            260                 265                 270

Lys Phe Lys Phe Lys Pro Asp Glu Lys Lys Ser Lys Tyr Tyr Thr Pro
        275                 280                 285

Glu Thr Gln Thr Glu Val Tyr Ala Tyr His Pro Lys Leu Gly Glu Trp
    290                 295                 300
```

-continued

```
Ile Glu Val Ala Thr Phe Gly Val Tyr Ser Pro Ile Ala Leu Ala Lys
305                 310                 315                 320

Tyr Asn Ile Asp Val Pro Val Met Asn Leu Gly Leu Gly Val Glu Arg
            325                 330                 335

Leu Ala Met Ile Ile Tyr Gly Tyr Glu Asp Val Arg Ala Met Val Tyr
            340                 345                 350

Pro Gln Phe Tyr Glu Tyr Arg Leu Ser Asp Arg Asp Ile Ala Gly Met
        355                 360                 365

Ile Arg Val Asp Lys Val Pro Ile Leu Asp Glu Phe Tyr Asn Phe Ala
    370                 375                 380

Asn Glu Leu Ile Asp Ile Cys Ile Ala Asn Lys Asp Lys Glu Ser Pro
385                 390                 395                 400

Cys Ser Val Glu Val Lys Arg Glu Phe Asn Phe Asn Gly Glu Arg Arg
            405                 410                 415

Val Ile Lys Val Glu Ile Phe Glu Asn Glu Pro Asn Lys Lys Leu Leu
            420                 425                 430

Gly Pro Ser Val Leu Asn Glu Val Tyr Val Tyr Asp Gly Asn Ile Tyr
        435                 440                 445

Gly Ile Pro Pro Thr Phe Glu Gly Val Lys Glu Gln Tyr Ile Pro Ile
    450                 455                 460

Leu Lys Lys Ala Lys Glu Glu Gly Val Ser Thr Asn Ile Arg Tyr Ile
465                 470                 475                 480

Asp Gly Ile Ile Tyr Lys Leu Val Ala Lys Ile Glu Glu Ala Leu Val
            485                 490                 495

Ser Asn Val Asp Glu Phe Lys Phe Arg Val Pro Ile Val Arg Ser Leu
            500                 505                 510

Ser Asp Ile Asn Leu Lys Ile Asp Glu Leu Ala Leu Lys Gln Ile Met
        515                 520                 525

Gly Glu Asn Lys Val Ile Asp Val Arg Gly Pro Val Phe Leu Asn Ala
    530                 535                 540

Lys Val Glu Ile Lys
545

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
gaattgaaac tgcatatgaa attaaaacat aaag                              34

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
cgcggatccc tattttatct caacctttg                                    29

<210> SEQ ID NO 6
<211> LENGTH: 45
<212> TYPE: DNA
<213> ORGANISM: Artificial Sequence
<220> FEATURE:
```

<223> OTHER INFORMATION: Primer

<400> SEQUENCE: 6
catatgcatc accatcacca tcacaaaaga aggatatag tgaag         45

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
agatcttcac ccccttaacc tg         22

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
agccatatta atggaattag aggggc         26

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
cgcggatcct tatttacaac tctca         25

<210> SEQ ID NO 10
<211> LENGTH: 37
<212> TYPE: DNA
<213> ORGANISM: Artificial Sequence
<220> FEATURE:
<223> OTHER INFORMATION: Primer

<400> SEQUENCE: 10
aattgaaact gcatatggtg tcatttacag ggtgtgt         37

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
cgcggatcct ccaagtgtat caaataaat         29

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
ctagctagca ttatcaaaac aaattacact ggag         34

```
<210> SEQ ID NO 13
<211> LENGTH: 34
<212> TYPE: DNA
<213> ORGANISM: Primer

<400> SEQUENCE: 13
cggggtaccc cagtcttttt aaatgtcgaa gtaa                                 34
```

US 7,723,069 B2

SITE SPECIFIC INCORPORATION OF PHOSPHOSERINE INTO POLYPEPTIDES USING PHOSPHOSERYL-TRNA SYNTHETASE

CROSS-REFERENCE TO RELATED APPLICATIONS

This application claims priority to U.S. Ser. No. 60/668,726 entitled "Site Specific Incorporation of Phosphoserine into Polypeptides: a System Utilizing the Phosphoseryl-tRNA Synthetase (SepRS) and its Cognate tRNA," filed in the U.S. Patent and Trademark Office on Apr. 5, 2005, by Dieter Soll and Jesse Rinehart.

STATEMENT REGARDING FEDERALLY FUNDED RESEARCH

The Federal Government has certain rights in the invention disclosed herein by virtue of Grant No. GM22854 from the National Institute of Health to Dieter Soll and Grant No. DE-FG02-98ER20311 from the Department of Defense to Dieter Soll.

FIELD OF THE INVENTION

The field of the present invention generally relates to methods for the site specific phosphorylation of proteins or peptides in vitro and in vivo.

BACKGROUND OF THE INVENTION

Signal transduction is any process by which a cell converts one kind of signal or stimulus into another. Processes referred to as signal transduction often involve a sequence of biochemical reactions inside the cell, which are carried out by enzymes and linked through second messengers.

Signal transduction is often accomplished by the activation of enzymes that can act upon other enzymes and change their catalytic activity. This may lead to increases or decreases in the activity of certain metabolic pathways, or may lead to even large intracellular changes, for example, the initiation of specific patterns of gene expression and/or changes in cell proliferation.

The most common covalent modification used in signal transduction processes is phosphorylation, which results in the alteration of the activity of those enzymes which become phosphorylated. Phosphorylation is the addition of a phosphate (PO4) group to a protein or a small molecule. Any of several amino acids in a protein may be phosphorylated. Phosphorylation on serine is the most common, followed by threonine. Tyrosine phosphorylation is relatively rare. However, since tyrosine phosphorylated proteins are relatively easy to purify using antibodies, tyrosine phosphorylation sites are relatively well understood. Histidine and aspartate phosphorylation occurs in prokaryotes as part of two-component signaling.

Other types of phosphorylation include oxidative phosphorylation. ATP, the "high-energy" exchange medium in the cell, is synthesized in the mitochondrion by addition of a third phosphate group to ADP in a process referred to as oxidative phosphorylation. ATP is also synthesized by substrate level phosphorylation during glycolysis. ATP is synthesized at the expense of solar energy by photophosphorylation in the chloroplasts of plant cells.

Phosphorylation of sugars is often the stage of their catabolism. It allows cells to accumulate sugars because the phosphate group prevents the molecules from diffusing back across their transporter.

In eukaryotes, protein phosphorylation is probably the most important regulatory event. Many enzymes and receptors are switched "on" or "loff" by phosphorylation and dephosphorylation. Phosphorylation is catalyzed by enzymes known as ATP-dependent phosphotransferases which are often simply referred to as "kinases." These include, among others, protein kinases, lipid kinases, inositol kinases, non-classical protein kinases, histidine kinases, aspartyl kinases, nucleoside kinases, and polynucleotide kinases.

The network underlying phosphorylation can be very complex. In some cellular signalling pathways, a protein A phosphorylates B, and B phosphorylates C, but A also phosphorylates C directly, and B can phosphorylate D, which may in turn phosphorylate A.

Phosphorylation regulates protein function by affecting conformation, for example. This in turn regulates such processes as enzyme activity, protein-protein interactions, sub-cellular distribution, and stability and degradation. The stoichiometry of phosphorylation of a given site is controlled by the relative activities of a cell's repertoire of protein kinases and phosphatases. Thus phosphorylation can often generate extremely rapid and reversible changes in the activity of target proteins. The ability to assay the state of phosphorylation of specific proteins is of great utility in the quest to establish the function of a given protein. Such assays are also critical for the identification of drugs that can influence the phosphorylation, and hence the function, of specific proteins.

In general, phosphoproteins are highly unstable and difficult to produce, both in terms of specific phosphorylation of biologically relevant amino acids and subsequent purification of protein. A means to specify and drive a targeted phosphorylation event with a high degree of certainty and efficiency in vivo has not been described.

Therefore, it is an object of the present invention to provide a method for the site specific phosphorylation of proteins or peptides.

It is further an object of the present invention to provide a method for the site specific phosphorylation of proteins or peptides in vivo.

BRIEF SUMMARY OF THE INVENTION

Nucleic acids encoding genes with SepRS and tRNASep activity are described. In a preferred embodiment, the "tRNASep" and "SepRS" refer to the cysteinyl-tRNA from *Methanocaldococcus jannaschii* (SEQ ID No. 1) and the class II-type O-phosphoseryl-tRNA synthetase from *Methanocaldococcus jannaschii* (SEQ ID No. 2), respectively and variants thereof having conservative substitutions, additions, and/or deletions therein not affecting the structure or function. Typically, SepRS preferentially aminoacylates tRNASep with O-phosphoserine and the tRNASep recognizes at least one codon. In a preferred embodiment, the tRNASep recognizes a stop codon or an unconventional or non-native codon.

Methods for producing proteins that contain at least one phosphoserine are described. The method results in proteins that have a phosphoserine incorporated into a protein in a manner indistinguishable from the phosphorylation of a serine by a kinase. Nucleic acids encoding genes with SepRS and tRNASep activity are provided, preferably on vectors, such as cloning vectors and expression vectors. These vectors can be in the form of a plasmid, a bacterium, a virus, a naked polynucleotide, or a conjugated polynucleotide. In one embodiment, the vectors are expressed in cells such as bacterial cells (e.g., *Escherichia coli*), archeaebacterial cells, and eukaryotic cells (e.g., yeast cells, mammalian cells, plant cells, insect cells, fungal cells). In an alternative embodiment, the vectors are expressed in an in vitro transcription/translation system. In this embodiment the vectors are transcribed and translated prior to or along with nucleic acids encoding one or more proteins or polypeptides.

In one aspect, the protein(s) or polypeptide(s) containing phosphoserine are produced and modified in a cell-dependent manner. This provides for the production of proteins that are stably folded, glycosylated, or otherwise modified by the cell.

Kits for producing polypeptides and/or proteins containing phosphoserine are also provided.

The proteins or polypeptides containing phosphoserine and antibodies to such polypeptides or proteins have a variety of uses including, the study of kinases, phosphotases, and target proteins in signal transduction pathways, antibody production, protein array manufacture and development of cell-based screens for new drug discovery and the development of therapeutic agents, agricultural products, or peptide-based libraries such as phage display libraries.

DETAILED DESCRIPTION OF THE INVENTION

Definitions

Figure 1:
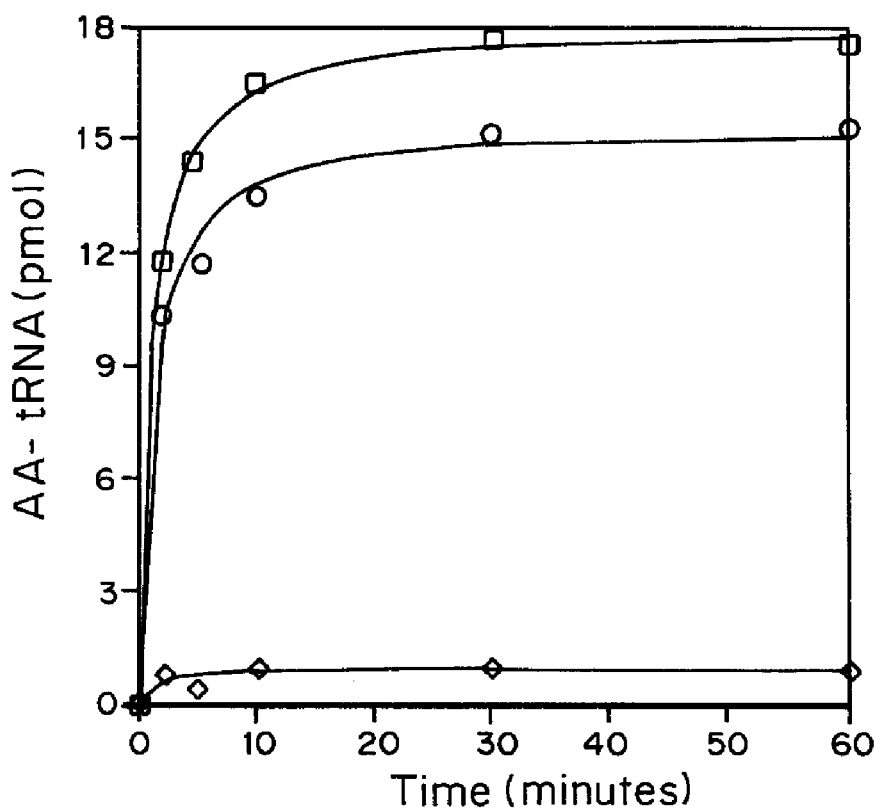
FIG. 1 is a graph of the amino acid specificity of *M. jannaschii* SepRS. Aminoacylation by the recombinant *M. jannaschii* SepRS was tested with the filter binding assay. *M. jannaschii* unfractionated tRNA charged with Sep (squares), total *M. maripaludis* tRNA and *M. jannaschii* SepRS incubated with Sep (circles), or with a 20-amino acid mixture (diamonds).

Aminoacyl-tRNA Synthetases ("AARS") are enzymes that charge (acylate) tRNAs with amino acids. These charged aminoacyl tRNAs then participate in mRNA translation and protein synthesis. The AARS show high specificity for charging a specific tRNA with the appropriate amino acid, for example, valyl-tRNA with valine by valyl-tRNA synthetase or tryptophanyl-tNRA with tryptophan by tryptophanyl-tRNA synthetase. In general, there is at least one AARS for each of the twenty amino acids.

Transfer RNA or tRNA refers to a set of genetically encoded RNAs that act during protein synthesis as adaptor molecules, matching individual amino acids to their corresponding codon on a messenger RNA (mRNA). In higher eukaryotes such as mammals, there is at least one tRNA for each of the 20 naturally occurring amino acids. In eukaryotes, including mammals, tRNAs are encoded by families of genes that are 73 to 150 base pairs long. tRNAs assume a secondary structure with four base paired stems known as the cloverleaf structure. The tRNA contains a stem and an anticodon. The anticodon is complementary to the codon specifying the tRNA's corresponding amino acid. The anticodon is in the loop is opposite the stem containing the terminal nucleotides. The 3' end of a tRNA is aminoacylated with a tRNA synthetase so that an amino acid is attached to the 3'end of the tRNA. This amino acid is delivered to a growing polypeptide chain as the anticodon sequence of the tRNA reads a codon triplet in an mRNA.

As used herein, "tRNASep" and "SepRS" refer to the cysteinyl-tRNA from *Methanocaldococcus jannaschii* (SEQ ID No. 1) and the class II-type O-phosphoseryl-tRNA synthetase from *Methanocaldococcus jannaschii* (whose nuceic acid sequence is SEQ ID No. 2, and the amino acid sequence is SEQ ID No. 3), respectively and variants thereof including conservative substitutions, additions, and deletions therein not affecting the structure or function, biologically active sequence variants of tRNASep and SepRS and in vitro generated covalent derivatives of tRNASep and SepRS that demonstrate tRNASep and SepRS activity.

Sequence variants of tRNASep and SepRS fall into one or more of three classes: substitutional, insertional and/or deletional variants. Sequence variants of tRNASep include nucleotide variants, while sequence variants of SepRS include nucleotide and/or amino acid variants. Insertions include amino and/or carboxyl terminal fusions as well as intrasequence insertions of single or multiple residues. tRNASep and SepRS include, for example, hybrids of mature tRNASep and SepRS with nucleotides or polypeptides, respectively, that are homologous with tRNASep and SepRS. tRNASep and SepRS also include hybrids of tRNASep and SepRS with nucleotides or polypeptides, respectively, homologous to the host cell but not to tRNASep and SepRS, as well as nucleotides or polypeptides heterologous to both the host cell and tRNASep and SepRS. Fusions include amino or carboxy terminal fusions with either prokaryotic nucleotides or peptides or signal peptides of prokaryotic, yeast, viral or host cell signal sequences.

Insertions can also be introduced within the mature coding sequence of tRNASep and SepRS. These, however, ordinarily will be smaller insertions than those of amino or carboxyl terminal fusions, on the order of one to four residues.

Insertional sequence variants of tRNASep and SepRS are those in which one or more residues are introduced into a predetermined site in the target tRNASep or SepRS.

Deletion variants are characterized by the removal of one or more residues from the tRNASep or SepRS sequence. For SepRS, deletions or substitutions of cysteine or other labile residues may be desirable, for example in increasing the oxidative stability or selecting the preferred disulfide bond arrangement of SepRS. Deletions or substitutions of potential proteolysis sites, e.g. Arg Arg, are accomplished, for example, by deleting one of the basic residues or substituting one by glutaminyl or histidyl residues. Variants ordinarily are prepared by site specific mutagenesis of nucleotides in the DNA encoding the tRNASep and SepRS, thereby producing DNA encoding the variant, and thereafter expressing the DNA in recombinant cell culture. However, variant tRNASep and SepRS fragments may be prepared by in vitro synthesis. The variants typically exhibit the same qualitative biological activity as the naturally-occurring analogue, although variants also are selected in order to modify the characteristics of tRNASep and SepRS.

Substitutional variants are those in which at least one residue sequence has been removed and a different residue inserted in its place. Owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations are a feature of each sequence disclosed herein.

"Conservative variations" of a particular nucleic acid sequence refers to those nucleic acids which encode identical or essentially identical amino acid sequences, or, where the nucleic acid does not encode an amino acid sequence, to essentially identical sequences. Conservative substitution tables providing functionally similar amino acids are well known in the art. The following sets forth exemplary groups which contain natural amino acids that are "conservative substitutions" for one another. Conservative Substitution Groups 1 Alanine (A) Serine (S) Threonine (T); 2 Aspartic acid (D) Glutamic acid (E); 3 Asparagine (N) Glutamine (Q); 4 Arginine (R) Lysine (K); 5 Isoleucine (I) Leucine (L) Methionine (M) Valine (V); and 6 Phenylalanine (F) Tyrosine (Y) Tryptophan (W).

Substitutional changes in function or immunological identity can be made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in SepRS protein properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

While the site for introducing a nucleotide or amino acid sequence variation is predetermined, the mutation per se need not be predetermined. For example, in order to optimize the performance of a mutation at a given site, random mutagenesis may be conducted at the target codon or region and the expressed tRNA$^{SeP}$ and SepRS variants screened for the optimal combination of desired activity. Techniques for making substitution mutations at predetermined sites in DNA having a known sequence are well known.

Substitutions are typically of single residues; insertions usually will be on the order of about from 1 to 10 residues; and deletions will range about from 1 to 30 residues. Substitutions, deletion, insertions or any combination thereof may be combined to arrive at a final construct. The mutations that will be made in the DNA encoding the variant SepRS must not place the sequence out of reading frame and preferably will not create complementary regions that could produce secondary mRNA structure.

A DNA isolate is understood to mean chemically synthesized DNA, cDNA or genomic DNA with or without the 3' and/or 5' flanking regions. DNA encoding tRNASep or SepRS can be obtained from other sources than *Methanocaldococcus jannaschii* by screening a cDNA library from cells containing mRNA using hybridization with labeled DNA encoding *Methanocaldococcus jannaschii* tRNASep or SepRS or fragments thereof (usually, greater than 100 bp).

As used herein proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTP and BLASTN using default parameters) are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Alignment of sequences for comparison can be conducted by many well-known methods in the art, for example, by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by the Gibbs sampling method (Chatterji and Pachter, *J. Comput Biol.* 12(6):599-608 (2005)), by PSI-BLAST-ISS (Margelevicius and Venclovas, *BMC Bioinformatics* 21;6:185 (2005)), or by visual inspection.

One algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (www.ncbi.nlm.nih.gov).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

As used herein "suppressor tRNA" refers to a tRNA that alters the reading of a messenger RNA (mRNA) in a given translation system. For example, a suppressor tRNA can read through a stop codon.

As used herein the "anticodon" is any combination of 2, 3, 4, and 5 bases (G or A or U or C) that are complementary to a "stop codon" of equivalent and complementary base composition. Known "stop codons" include but are not limited to, the three codon bases, UAA known as ochre, UAG known as amber and UGA known as opal that do not code for an amino acid but act as signals for the termination of protein synthesis. Generally the anticodon loop consists of seven nucleotides. In the 5'0 to 3' direction the first two positions 32 and 33 precede the anticodon positions 34 to 36 followed by two nucleotides in positions 37 and 38 (Alberts, B., et al. in *The Molecualr Biology of the Cell*, 4$^{th}$ ed, Garland Science, New York, N.Y. (2002)). The size and nucleotide composition of the anticodon is generally the same as the size of the codon with complementary nucleotide composition codon. A four base pair codon would consist of four bases such as 5'-AUGC-3' and an anticodon for such a codon would complement the codon such that the tRNA contained 5'-GCAU-3' with the anticodon starting at position 34 of the tRNA. A 5 base codon 5'-CGGUA-3' codon is recognized by the 5'-UACCG-3' anticodon (Hohsaka T., et al. *Nucleic Acids Res.* 29:3646-3651 (2001)). The composition of any such anticodon for 2 (16=any possible combination of 4 nucleotides), 3 (64), 4 (256), and 5 (1024) base codons would follow the same logical composition. The "anticodon" typically starts at position 34, but may also reside in any position of the "anti-codon stem-loop" such that the resulting tRNA is complementary the "stop codon" of equivalent and complementary base. composition.

As used herein "translation system" refers to the components necessary to incorporate a naturally occurring amino acid into a growing polypeptide chain (protein). Components of a translation system can include, e.g., ribosomes, tRNAs, synthetases, mRNA and the like. The components described herein can be added to a translation system, in vivo or in vitro. A translation system can be either prokaryotic, e.g., an *E. coli* cell, or eukaryotic, e.g., a yeast, mammalian, plant, or insect or cells thereof.

A "transgenic organism," as used herein, is any organism, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. Suitable transgenic organisms include, but are not limited to, bacteria, cyanobacteria, fungi, plants and animals. The nucleic acids described herein can be introduced into the host by methods known in the art, for example infection, transfection, transformation or transconjugation. Techniques for transferring DNA into such organisms are widely known and provided in references such as Sambrook, et al. (1989) Molecular Cloning: A Laboratory Manual, 2$^{nd}$ ed., vol. 1-3, Cold Spring Harbor Press, Plainview N.Y.

As used herein, the term "eukaryote" or "eukaryotic" refers to organisms or cells or tissues derived therefrom belonging to the phylogenetic domain Eukarya such as animals (e.g., mammals, insects, reptiles, and birds), ciliates, plants (e.g., monocots, dicots, and algae), fungi, yeasts, flagellates, microsporidia, and protists.

As used herein, the term "non-eukaryotic organism" refers to organisms including, but not limited to, organisms of the Eubacteria phylogenetic domain, such as *Escherichia coli*, *Thermus thermophilus*, and *Bacillus stearothermophilus*, or organisms of the Archaea phylogenetic domain such as, *Methanococcus jannaschii*, *Methanobacterium thermoautotrophicum*, Halobacterium such as *Haloferax volcanii* and Halobacterium species NRC-1, *Archaeoglobus fulgidus*, *Pyrococcus furiosus*, *Pyrococcus horikoshii*, and *Aeuropyrum pernix*.

A. General Molecular Biology Techniques

Various types of mutagenesis can be used to modify a nucleic acid encoding a gene with tRNA$^{SeP}$ activity to recognize a stop codon or any other codon of choice. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, and mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis and double-strand break repair.

B. Methods for Producing Proteins Containing Phosphoserine

Suitable nucleic acids include any nucleic acids encoding genes with SepRS and tRNASep activity. In one embodiment, the "tRNASep" and "SepRS" refer to the cysteinyl-tRNA from *Methanocaldococcus jannaschii* (SEQ ID No. 1) and the class II-type O-phosphoseryl-tRNA synthetase from *Methanocaldococcus jannaschii* (SEQ ID No. 2), respectively and variants thereof including conservative substitutions, additions, and deletions therein not affecting the structure or function. However, any nucleic acid encoding genes with SepRS and tRNASep activity are suitable for use in the methods described herein. For example, SEQ ID Nos. 1 and 2 can be used to identify other genes with tRNASep and SepRS activity by a number of methods known to those of skill in the art including, but not limited to, searching for genes with homology to SEQ ID Nos. 1 and 2. Additionally, these sequences can be used to engineer other genes with tRNASep and/or SepRS activity. Finally, other known tRNAs and aminoacyl-tRNA synthetases or transferases can be screened for tRNASep and SepRS activity, respectively.

i) In vitro Transcription/Translation

In one embodiment, the genes encoding tRNA$^{SeP}$ or SepRS activity are synthesized in vitro prior to or along with transcription and translation of one or more target protein(s). The synthesis of protein from a DNA sequence in vitro takes two steps. The first is transcription of an RNA copy and the second is the translation of a protein.

In vitro protein synthesis does not depend on having a polyadenylated RNA, but if having a poly(A) tail is essential for some other purpose a vector may be used that has a stretch of about 100 A residues incorporated into the polylinker region. That way, the poly(A) tail is "built in" by the synthetic method.

Eukaryotic ribosomes read RNAs more efficiently if they have a 5' methyl guanosine cap. RNA caps can be incorporated by initiation of transcription using a capped base analogue, or adding a cap in a separate in vitro reaction post-transcriptionally.

Combined transcription/translation systems are available, in which both phage RNA polymerases (such as T7 or SP6) and eukaryotic ribosomes are present. One example of a kit is the TNT® system from Promega Corporation.

Other suitable in vitro transcription/translation systems include, but are not limited to, the rabbit reticulocyte system, the E. coli S-30 transcription-translation system, and the wheat germ based translational system.

ii) In vivo Methods

Host cells and organisms can also incorporate phosphoserine into proteins or polypeptides via genes encoding tRNA$^{Sep}$ or SepRS activity.

Genes encoding tRNA Sep and SepRS are introduced into cells or organisms, which, when expressed, will function as a normal tRNA/tRNA synthetase pair to incorporate phosphoserine into proteins or polypeptides. Suitable organisms include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. (See, e.g., Van Heeke and Schuster (1989) J. Biol. Chem. 264:5503-5509; Engelhard, et al. (1994) Proc. Natl. Acad. Sci. USA 91:3224-3227; Sandig, et al. (1996) Hum. Gene Ther. 7:1937-1945; Takamatsu, (1987) EMBO J. 6:307-311; The McGraw Hill Yearbook of Science and Technology (1992) McGraw Hill, New York N.Y., pp. 191-196; Logan, J. and T. Shenk (1984) Proc. Natl. Acad. Sci. USA 81:3655-3659; and Harrington, J. J. et al. (1997) Nat Genet 15:345-355.) It will be understood by one of ordinary skill in the art that regardless of the system used (i.e. in vitro or in vivo), expression of genes encoding tRNA$^{Sep}$ or SepRS activity will result in site specific incorporation of phosphoserine into the target polypeptides or proteins that are translated in the system. Host cells are genetically engineered (e.g., transformed, transduced or transfected) with the vectors encoding tRNA$^{Sep}$ and SepRS, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., Proc. Natl. Acad. Sci. USA 82, 5824 (1985), infection by viral vectors, high velocity ballistic penetration by small particles with the nucleic acid either within the matrix of small beads or particles, or on the surface (Klein et al., Nature 327, 70-73 (1987)). Such vectors can optionally contain one or more promoter. A "promoter" as used herein is a DNA regulatory region capable of initiating transcription of a gene of interest. Some promoters are "constitutive," and direct transcription in the absence of regulatory influences. Some promoters are "tissue specific," and initiate transcription exclusively or selectively in one or a few tissue types. Some promoters are "inducible," and achieve gene transcription under the influence of an inducer. Induction can occur, e.g., as the result of a physiologic response, a response to outside signals, or as the result of artificial manipulation. Some promoters respond to the presence of tetracycline; "rtTA" is a reverse tetracycline controlled transactivator. Such promoter are well known to those of skill in the art.

Kits are commercially available for the purification of plasmids from bacteria, (see, e.g., GFX™ Micro Plasmid Prep Kit from GE Healthcare; Strataprep® Plasmid Miniprep Kit and StrataPrep® EF Plasmid Midiprep Kit from Stratagene; GenElute™ HP Plasmid Midiprep and Maxiprep Kits from Sigma-Aldrich, and, Qiagen plasmid prep kits and QIAfilter™ kits from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems.

Prokaryotes useful as host cells include, but are not limited to, gram negative or gram positive organisms such as E. coli or Bacilli. In a prokaryotic host cell, a polypeptide may include an N-terminal methionine residue to facilitate expression of the recombinant polypeptide in the prokaryotic host cell. The N-terminal Met may be cleaved from the expressed recombinant polypeptide. Promoter sequences commonly used for recombinant prokaryotic host cell expression vectors include lactamase and the lactose promoter system.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence are inserted into the pBR322 vector. Other commercially available vectors include, for example, T7 expression vectors from Invitrogen, pET vectors from Novagen and pALTER® vectors and PinPoint® vectors from Promega Corporation.

Yeasts useful as host cells include, but are not limited to, those from the genus Saccharomyces, Pichia, K. Actinomycetes and Kluyveromyces. Yeast vectors will often contain an origin of replication sequence, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, (1980)) or other glycolytic enzymes (Holland et al., Biochem. 17:4900, (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase; triosephosphate isomerase, phosphoglucose isomerase, and glucokinase. Other suitable vectors and promoters for use in yeast expression are further described in Fleer et al., Gene, 107:285-195 (1991), in Li, et al., *Lett Appl Microbiol.* 40(5):347-52 (2005), Jansen, et al., *Gene* 344:43-51 (2005) and Daly and Heam, *J. Mol. Recognit.* 18(2):119-38 (2005). Other suitable promoters and vectors for yeast and yeast transformation protocols are well known in the art.

Mammalian or insect host cell culture systems well known in the art can also be employed to express recombinant tRNA$^{Sep}$ and SepRS for producing proteins or polypeptides containing phosphoserine. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

C. Purifying Proteins Containing Phosphoserine

Proteins or polypeptides containing phosphoserine can be purified, either partially or substantially to homogeneity, according to standard procedures known to and used by those of skill in the art including, but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against proteins containing phosphoserine are used as purification reagents, e.g., for affinity-based purification of proteins containing phosphoserine. Once purified, partially or to homogeneity, as desired, the polypeptides are optionally used e.g., as assay components, therapeutic reagents or as immunogens for antibody production.

A variety of purification/protein folding methods are well known in the art, including, e.g., those set forth in Deutscher, Methods in Enzymology Vol. 182: Guide to Protein Purification, Academic Press, Inc. N.Y. (1990); Sandana (1997) Bioseparation of Proteins, Academic Press, Inc.; Bollag et al. (1996) Protein Methods, 2nd Edition Wiley-Liss, NY; Janson and Ryden (1998) Protein Purification: Principles, High Resolution Methods and Applications, Second Edition Wiley-VCH, NY; Walker (1998) Protein Protocols on CD-ROM Humana Press, NJ; and Hardin (2001) Cloning, Gene Expression and Protein Purification: Experimental Procedures and Process Rationale, Oxford University Press, Oxford, England.

As noted, those of skill in the art will recognize that, after synthesis, expression and/or purification, proteins can possess a conformation different from the desired conformations of the relevant polypeptides. For example, polypeptides produced by prokaryotic systems often are optimized by exposure to chaotropic agents to achieve proper folding. During purification from lysates derived from *E. coli*, the expressed protein is optionally denatured and then renatured. This is accomplished by soubilizing the proteins in a chaotropic agent such as guanidine HCl.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art (see, the references above, and Debinski, et al. (1993) *J. Biol. Chem.,* 268: 14065-14070; Kreitman and Pastan (1993) *Bioconjug Chem.,*4: 581-585; and Buchner, et al., (1992) *Anal. Biochem.,* 205: 263-270). Debinski, et al., for example, describe the denaturation and reduction of inclusion body proteins in guanidine-DTE. The proteins can be refolded in a redox buffer containing, e.g., oxidized glutathione and L-arginine. Refolding reagents can be flowed or otherwise moved into contact with the one or more polypeptide or other expression product, or vice-versa.

E. Methods of Use

Proteins or polypeptides containing phosphoserine and antibodies that bind to such proteins produced by the methods described herein can be used for research involving phosphoproteins such as the study of kinases, phosphotases, and target proteins in signal transduction pathways. Proteins or polypeptides containing phosphoserine produced by the methods described herein can also be used for antibody production, protein array manufacture and development of cell-based screens for new drug discovery.

F. Kits

Kits for producing polypeptides and/or proteins containing phosphoserine are also provided. For example, a kit for producing a protein that contains phosphoserine in a cell is provided, where the kit includes a polynucleotide sequence encoding tRNA$^{Sep}$ and a polynucleotide sequence encoding SepRS. In one embodiment, the kit further includes phsophoserine. In another embodiment, the kit further comprises instructional materials for producing the protein. In another embodiment, a kit for producing a protein that contains phosphoserine in vitro is provided, where the kit includes a polynucleotide sequence encoding tRNA$^{Sep}$, a polynucleotide sequence encoding SepRS, and phsophoserine. In another embodiment, the kit further comprises instructional materials for producing the protein in vitro.

The present invention will be further understood by reference to the following non-limiting examples.

EXAMPLES

Example 1

Identification of Genes Encoding tRNASep and SepRS Activity

Several methanogenic archaea lack cysteinyl-transfer RNA (tRNA) synthetase (CysRS), the essential enzyme-that provides Cys-tRNACys for translation in most organisms. Partial purification of the corresponding activity from *Methanocaldococcus jannaschii* indicated that tRNACys becomes acylated with O-phosphoserine (Sep) but not with cysteine. Further analyses identified a class II-type O-phosphoseryl-tRNA synthetase (SepRS) and Sep-tRNA:Cys-tRNA synthase (SepCysS). SepRS specifically forms Sep-tRNACys, which is then converted to Cys-tRNACys by SepCysS. Comparative genomic analyses suggest that this pathway, encoded in all organisms lacking CysRS, can also act as the sole route for cysteine biosynthesis. This was proven for *Methanococcus maripaludis*, where deletion of the SepRS-encoding gene resulted in cysteine auxotrophy. As the conversions of SeptRNA to Cys-tRNA or to selenocysteinyl-tRNA are chemically analogous, the catalytic activity of SepCysS provides a means by which both cysteine and selenocysteine may have originally been added to the genetic code.

The translation of cysteine codons in mRNA during protein synthesis requires cysteinyl-tRNA (Cys-tRNA$^{Cys}$). Cys-tRNA$^{Cys}$ is normally synthesized from the amino acid cysteine and the corresponding tRNA isoacceptors (tRNA$^{Cys}$) in an adenosine triphosphate (ATP)dependent reaction catalyzed by cysteinyl-tRNA synthetase (CysRS). Genes encoding CysRS, cysS, have been detected in hundreds of organisms encompassing all three living domains (Li et al., *FEBS Lett.* 462, 302 (1999)). The only exceptions are certain methanogenic archaea, the completed genome sequences of which encode no open reading frames (ORFs) with obvious homology to known cysS sequences (Li et al., *FEBS Lett.* 462, 302 (1999)). Because of the discovery that the genomes of a number of methanogenic archaea either lack cysS (*Methanocaldococcus jannaschii, Methanothermobacter thermautotrophicus*, and *Methanopyrus kandleri*) or can dispense with it (*Methanococcus maripaludis*), the formation of Cys-tRNA$^{Cys}$ in these organisms has been a much studied and increasingly contentious topic (Ruan et al., *J. Bacteriol.* 186, 8 (2004) and Ambrogelly et al., *Cell. Mol. LifeSci.* 61, 2437 (2004)). A noncognate aminoacyl-tRNA synthetase [aaRS (Stathopoulos et al., *Science* 287, 479 (2000); Lipman, et al., *Biochemistry* 39, 7792 (2000); and Zhang and Hou, *RNA Biol.* 1, 35 (2004))] and a previously unassigned ORF (Fabrega et al., *Nature* 411, 110 (2001)) were variously implicated in Cys-tRNA$^{Cys}$ formation. Recent studies failed to provide conclusive support for either of these routes, leaving the mechanism of Cys-tRNA$^{Cys}$ formation still in doubt (Ruan et al., *J. Bacteriol.* 186, 8 (2004)).

i. Materials and Methods a) General

*M. jannaschii* (DSM 2661) cells were a gift of Karl Stetter and Michael Thomm, Archaeenzentrum, Universitait Regensburg, Germany. Cells were grown anaerobically in a 300 L fermentor on H2 and C02 (80:20) at 85° C. under a pressurized headspace of 200 kPa as described (Tomari, et al., *Genes Cells* 5, 689 (2000)). Cells were harvested at the mid point of exponential growth phase and stored at −80° C. *E. coli* BL21/pQE30 producing His6-tagged *E. coli* terminal tRNA nucleotidyl transferase was a gift from T. Ueda (Tomari, et al., *Genes Cells* 5, 689 (2000)). *E. coli* BL21-CodonPlus (DE3)-RIL and BL21-RIL strains were from Stratagene. Ni-NTA agarose was from Qiagen (Chatsworth, Calif.) and BD Talon metal affinity resin from BD Bioscience. The pET15b and pET11b vectors were from Novagen. Oligonucleotide synthesis and DNA sequencing was performed by the Keck Foundation Biotechnology Resource Laboratory at Yale University. Uniformly labeled [14C] aa mixture (50 mCi/mmol), [14C]Asn (228.4 mCi/mmol), [14C]Cys (303 mCi/mmol), [14C]Met (57.9 mCi/mmol), [14C]Trp (53.8 mCi/mmol) and [14C]Gln (210 mCi/mmol) were from PerkinElmer, Boston. [γ-32P]ATP (6,000 Ci/mmol) was from Amersham Biosciences. [14C]Sep (50 mCi/mmol) was from American Radiolabeled Chemicals, St. Louis. *E. coli* phenylalanyl-tRNA synthetase and ATP-pyrophosphate exchange were described (Bentin et al., *J. Biol. Chem.* 279, 19839 (2004)).

b) Preparation of *M. jannaschii* Cell-free Extracts

Cell lysis and all chromatography steps were carried out under anaerobic conditions (90% N2, 5% CO2, and 5% H2) in a Bactron X chamber (Sheldon Manufacturing Inc.). Solutions were saturated with N2 prior to use unless otherwise indicated. Frozen *M. jannaschii* cells (50 g) were resuspended in 3 volumes of buffer A (20 mM Tris-HCl pH 8, 10 mM DTT, 5 mM NaCl, 0.1 mM ZnCl2). Cells were disrupted by a single passage through a French press at 10.34 MPa. Cell debris and the insoluble protein fraction were removed by centrifugation for 60 min at 100,000×g at 4° C.

c) Chromatographic Enrichment of Cysteinyl-tRNA Synthesis Activity

*M. jannaschii* cell-free extract was dialyzed overnight against buffer A and loaded on a DE52 DEAE-cellulose (Whatman) column (100 ml) previously equilibrated with buffer A. The column was washed with 10 column volumes buffer A to remove unbound protein. Bound proteins were eluted by gravity flow using a gradient of 0.005-0.5 M NaCl in buffer A. Active fractions were pooled and loaded on a HiTrap Heparin HP (5 ml) column (Amersham) previously equilibrated with buffer B (20 mM Tris-HCl pH 8, 10 mM DTT, 150 mM NaCl, 0.1 mM ZnCl2), and active fractions were eluted using a gradient of 0.15-0.7 M NaCl in buffer B. After dialysis against buffer C (20 mM Tris-HCl pH 7.5, 10 mM DTT, 10 mM NaCl, 0.1 mM ZnCl2) the active fractions were applied to a 1 ml MonoS column (Amersham) equilibrated with buffer C and eluted with a linear gradient from 0.01-1 M NaCl in buffer C. Alternatively, the active Heparin fractions were dialyzed with buffer B and applied on a 1 ml MonoQ column (Amersham) equilibrated with buffer B and eluted with a linear gradient of 0.15-0.7 M NaCl in buffer B. Active as well as certain inactive MonoS and MonoQ fractions were analyzed using Multidimensional Protein Identification Technology (see below).

d) Solid-phase Extraction and Column Chromatography of Low-molecular-weight Fraction All steps were carried out under aerobic conditions. *M. jannaschii* S-100 was filtered with a YM-3 centriprep (Millipore) membrane with a molecular weight cut off (MWCO) of 3 kD. Filtrate, 1 ml, was diluted with 8.8 ml H2O and 0.2 ml 30% ammonium hydroxide and applied to a MAX 6-cc column (Oasis) previously equilibrated with 5 ml methanol and then with 5 ml H2O. The column was washed with 5 ml 100% methanol and the active fraction eluted with 5 ml of 50 mM. ammonium acetate pH 7, 5% methanol. The active fraction was diluted with 1 volume of 8% formic acid and applied to a MCX 6-cc column (Oasis) previously equilibrated with 5 ml methanol and then with 5 ml H2O. The active flow-through was neutralized with 30% ammonium hydroxide, lyophilized, dissolved in 0.2 ml water and applied to a Superdex Peptide 10/300 (Amersham) previously equilibrated with 0.1 M ammonium acetate pH 7. Active fractions were lyophilized and sent for liquid chromatography and mass spectrometry analyses.

e) Assay for CysRS Activity

Cys-tRNACys formation was determined by acid urea gel electrophoresis and Northern blot analysis as described (Varshney, et al., *J. Biol. Chem.* 266, 24712 (1991) and Polycarpo et al., *Mol. Cell* 12, 287 (2003)). The 75 μl reaction mixture contained 20 mM Tris-HCl pH 8, 50 mM NaCl, 10 mM DTT, 0.2 mM ZnCl2, 1 mg/ml unfractionated *M. maripaludis* tRNA, 0.1 volumes protein fraction and 0.5 volumes of a *M. jannaschii* low-molecular-weight filtrate (MWCO <3 kD) (see above). The reaction mixture was incubated for 15 min at 55° C., quenched with 10 μl 3 M sodium acetate pH 4.5 and extracted with acidic phenol. The aqueous phase was applied to a MicroSpin G25 column (Amersham) and the eluted aa-tRNA ethanol precipitated. The aa-tRNA was dissolved in 10 mM sodium acetate pH 4.5 to a final concentration of 3 mg/ml. Half of an RNA aliquot was left untreated and the other half was deacylated by mild alkaline hydrolysis with Tris base (0.1 M Tris pH9, 30 min, 37° C.). 1 μl of tRNA sample was mixed with 1.5 µl loading buffer (7 M urea, 0.3 M sodium acetate pH 4.5, 10 mM EDTA, 0.1% bromophenol blue, 0.1% xylene cyanol) and loaded on a 9% polyacrylamide gel (50×20 cm, 0.4 mm thick) containing 7 M urea, 0.1 M sodium acetate pH 5, and run at 4° C., 550 V in 0.1 M sodium acetate pH 5 for 40 hours. Detection of the tRNAs was performed by Northern blotting. The portion of the gel, which contained the tRNAs of interest, was blotted onto a HybondN+ membrane (Amersham) using a Hoefer Electroblot apparatus (Amersham) at 20 V for 2 hours with 20 mM Tris-acetate pH 7.8, 5 mM sodium acetate pH 7 and 0.2 mM EDTA as transfer buffer. The membrane was cross-linked to tRNA by 254 nm irradiation with a UV Stratalinker™ 2400 (Stratagene). The tRNAs were detected by hybridization with a 5'32P-labeled oligodeoxyribonucleotide probe. The probes were complementary to nucleotides 1-23 of tRNACys, and 1-25 of tRNASec, respectively.

f) Cloning of the *M. jannaschii* sepS Gene and Purification of SepRS

*M. jannaschii* genomic DNA was used as template. The sepS ORF (accession no. NP_248670) was amplified by PCR using the primers 5'-GAATTGAAACTGCATAT-GAAATTAAAACATAAAG-3' (SEQ ID No. 4) and 5'-CGCGGATCCCTATTTTATCTCAACCTTTG-3' (SEQ ID No. 5). The resulting DNA fragment was digested with NdeI and BamHI and inserted into the pET15b vector at the NdeI and BamHI sites for expression of N-terminal His6-tagged proteins in the *E. coli* BL21-CodonPlus (DE3)-RIL strain. Cultures were grown aerobically at 37° C. in LB medium supplemented with 100 µg/ml ampicillin and 34 µg/ml chloramphenicol. When the cultures reached an A600 of 0.5, expression of His6-tagged protein was induced for 8 hours at 15° C. with the addition of 0.6 mM isopropyl-β-D-thiogalactoside (IPTG) before harvesting the cells. The enzyme was purified under aerobic conditions by Ni-nitrilotriacetic acid-agarose chromatography (Qiagen, Chatworth, Calif.) as suggested by the provider. Active fractions were pooled and dialyzed against 20 mM Tris-HCl pH 8, 50 mM NaCl, 5 mM DTT containing 30% glycerol and stored at 4° C.

g) Cloning of the *M. thermautotrophicus* sepS Gene and Purification of SepRS

*M. thermautotrophicus* ΔH genomic DNA was used as template. The sepS ORF (accession no. NP_276615) was amplified by PCR using the primers 5'-CATATGCATCAC-CATCACCATCACAAAAGAAAGGATATAGTGAA G-3' (SEQ ID No. 6) and 5'-AGATCTTCACCCCCTTAAC-CTG-3' (SEQ ID No. 7). The resulting DNA fragment was digested with NdeI and BglII and inserted into the pET11b vector at the NdeI and BamHI sites for expression of N-terminal His6-tagged proteins in the BL21-RIL strain. Cultures were grown aerobically at 37° C. in LB medium supplemented with 200 µg/ml ampicillin. When the cultures reached an A600 of 0.2, cells were cultivated for an additional 12 hours at room temperature. After harvesting, cells were resuspended in a buffer containing 50 mM sodium phosphate pH 8.0, 300 mM NaCl, 10 mM imidazole, 5 mM of 2-mercaptoethanol and Complete EDTA-free protease inhibitor cocktail (Roche) and disrupted by sonication. The N-terminal His6-tagged protein was purified by affinity chromatography on a BD TALON metal affinity resin (BD Biosciences) according to the procedure provided by the manufacturer. Fractions containing the protein were pooled and dialyzed against a buffer containing 10 mM potassium phosphate pH 7.0 and 5 mM 2-mercaptoethanol. The protein was then loaded onto a CHT5 hydroxyapatite column (Biorad) equilibrated with dialysis buffer. The elution was performed with a gradient from 10 to 500 mM potassium phosphate, pH 7. The fractions containing the protein were dialyzed against 50 mM Tris-HCl pH 8.0 and 5 mM 2-mercaptoethanol, and a second time against the same buffer with 50% glycerol.

h) SepRS Activity Assay

Sep-tRNACys formation was assayed aerobically in aminoacylation buffer (20 mM Tris-HCl pH8, 50 mM NaCl, 5 mM DTT, 20 mM MgCl2, 10 mM ATP, 0.2 mM [14C]Sep or [14C] 20 amino acid mixture) in the presence of 3 µM *M. jannaschii* His6-SepRS, by using 1 mg/ml unfractionated *M. maripaludis* or unfractionated *M. jannaschii* tRNA as substrate in a final volume of 0.1 ml. Aliquots of 18 µl from the reaction were removed periodically, spotted on Whatman 3 MM paper filter disks and washed three times in 10% trichloroacetic acid to remove free amino acid. After drying, the radioactivity was measured by liquid scintillation counting.

i) Preparation of Radiolabeled Total tRNA from *M. thermautotrophicus* tRNA-[32P]A76-3' was prepared using the ATP-PPi exchange reaction catalyzed by *E. coli* tRNA-terminal nucleotidyl transferase (Wolfson and Uhlenbeck, *Proc. Natl. Acad. Sci. U.S.A.* 99, 5965 (2002)), and then purified as follows. The exchange reaction media (25 µl) was quenched by addition of 250 µl of phenol/water (1:1) and the mix then directly applied to a G25 Sephadex column previously equilibrated with water. The tRNA was separated from any remaining ATP by chromatography on a HighTrap Q FF 1 ml column (Pharmacia) in a buffer containing 20 mM Tris-HCl pH 7.5 and 0.5 mM EDTA with a gradient of 0 to 1 M NaCl. ATP eluted at ~170 mM NaCl, the radiolabeled total tRNA at ~600 mM. The radioactive tRNA fractions were pooled and the tRNA precipitated, dried and resuspended in water.

j) Aminoacylation Reaction Analysis by TLC

Aminoacylation was performed at 37° C. in 100 mM Hepes pH 7.2, 30 mM KCl, 2 mM ATP, 1.8 mg/ml of total tRNA, a trace of tRNA-[32P]A76 (3500 cpm/µl), 66 µM Sep and 0.1 µM of His6-SepRS or without enzyme. At various times, an aliquot was removed and treated with RNase P1 as described previously (Wolfson and Uhlenbeck, *Proc. Natl. Acad. Sci. U.S.A.* 99, 5965 (2002)). The liberated [a-32P]AMP and Sep-[α-32P]AMP were separated by thin-layer chromatography (TLC) on cellulose (Merck) in isobutyric acid/25% ammoniac/water (50/1.1/28.9). Samples were quantified using a PhosphorImager (Molecular Dynamics).

k) Cloning of the MJ1678 Gene and Preparation of Sep-tRNACys:Cys-tRNACys Synthase (SepCysS)

*M. jannaschii* genomic DNA was used as template. The MJ1678 ORF (accession no. NP_248688) was amplified by PCR using the primers 5'-AGCCATATTAATGGAATTA-GAGGGGC-3' (SEQ ID No. 8) and 5'-CGCGGATCCT-TATTTACAACTCTCA-3' (SEQ ID No. 9). The resulting DNA fragment was digested with AseI and BamHI and inserted into the pET15b vector at the NdeI and BamHI sites for expression of N-terminal His6-tagged proteins in the *E. coli* BL21-CodonPlus (DE3)-RIL strain. Cultures were grown under aerobic conditions at 37° C. in LB medium, supplemented with 100 µg/ml ampicillin, 34 µg/ml chloramphenicol, and 0.01% pyridoxine. When the cultures reached A600 of 0.5, expression of His6-tagged protein was induced for 8 hours at 15° C. by addition of 0.6 mM IPTG before harvesting the cells. Cells were resuspended in buffer D (50 mM Hepes-NaOH pH 8, 50 mM NaCl, 10 mM DTT, 0.1 mM ZnCl2, 10 µM PLP) and disrupted by single passage through a French press at 1500 p.s.i. Cell debris and the insoluble protein fraction were removed by centrifugation for 60 min at 100,000 g at 4° C. The supernatant was dialyzed against the same buffer. Dialyzed cell-free extract was applied to a 1 ml Heparin column (Amersham) and active fractions were eluted with a linear gradient of 0.05-0.6 M NaCl in buffer D.

l) SepCysS Activity Assay

M. maripaludis [14C]Sep-tRNACys was prepared by using purified M. jannaschii SepRS as described above for the aminoacylation assay. At the end of the reaction, aminoacylated tRNA was isolated by phenol extraction and ethanol precipitation and used as substrate for the thiolation assay. The thiolation assay, performed for 15 min at 55° C. in a volume of 75 µl under strict anaerobic conditions, contained 50 mM HEPES-NaOH pH 8, 10 mM DTT, 20 mM MgCl2, 2 mM Na2S, and 0.2 volumes of recombinant SepCysS (heparin eluate, see above). As control E. coli S100 cell-free extract from cells containing the empty plasmid were used instead of SepCysS. The reaction was quenched with 10 µl 3 M. sodium acetate pH 4.5 and extracted with acidic phenol. The aqueous phase was applied to a MicroSpin G25 spin column (Amersham), and the eluted tRNA ethanol precipitated. The aminoacyl-tRNA was deacylated in 10 µl 200 mM NaOH at room temperature for 10 min. Cysteine was then oxidized to cysteic acid as described (Moore, J. Biol. Chem. 238, 235 (1963)) by adding 200 µl of ice cold 80% performic acid to the 10 µl deacylation mixture and incubating for 4 hours on ice. Oxidation was stopped by adding 30 µl 48% hydrobromic acid. After drying and resuspension in water, the samples were separated by TLC on cellulose plates (Sigma) in chloroform/methanol/water/ammonium hydoxide (6:6:1:2). The identity of the various species was also confirmed using a second solvent, n-propanol: water (7:3). After drying, the plate was exposed to a phosphorimaging plate (Fuji), in order to detect the labeled amino acids.

m) Protein Analysis by Multidimensional Protein Identification Technology (MudPIT)

I. Digestion of M. jannaschii complexes. After methanol/chloroform precipitation, protein pellets from selected MonoQ and MonoS fractions were resuspended in 50 µL of 100 mM ammonium bicarbonate buffer (pH 8.5). The proteins were sequentially denatured with 8 M urea, reduced with 5 mM TCEP at room temperature for 30 min, and carboxyamidomethylated using 10 mM IAM in the dark for 30 min. Proteins were then digested with endoproteinase Lys-C (1:200) overnight at 37° C. The digests were diluted 3-fold to 2 M urea by adding 100 mM NH4HCO3 (pH 8.5). $CaCl_2$ was added to 1 mM. Finally, porcine trypsin (1:100) was added to each sample, followed by incubation at 37° C. overnight. After incubation, 90% formic acid was added to 4% final concentration to quench the digestion reaction and protonize the peptides. Samples were stored at −20° C. until analysis.

II. Column packing and sample loading. A loading column was made by packing a fused-silica column (250 µm i.d., 365 µm o.d., Agilent) with 3 cm of a strong cation exchange resin (5 µm, 100 Å, Partisphere SCX, Whatman, Clifton, Calif.), followed by 2 cm of Polaris C 18 (5 µm, 100 Å, Metachem, Ventura, Calif.). A microfilter (Upchurch) was used as the frit. Then, a fused-silica capillary column (100 µm i.d., 365 µm o.d., Polytechnique) was pulled with a P-2000 laser puller (Sutter Instrument Co., Novato, Calif.). This fritless capillary column was packed with 9 cm of Polaris C18 as the separation column. The digested proteins were then loaded onto the loading column and washed with 5% ACN/0.1% formic acid to desalt. Finally, after sample loading and washing, the loading column was connected with the C18 separation column through the microfilter and the entire assembly used as a three-phase MudPIT column.

III. Multidimensional Protein Identification Technology. MudPIT analysis was performed similarly to the method described previously (Florens et al., Nature 419, 520 (2002) and Zhu, et al., J. Proteome Res. 3, 538 (2004)). A quarternary HPLC (Agilent 1100) was directly coupled to an LCQ ion trap mass spectrometer (Thermofinnigan, San José, Calif.) equipped with a nano-LC electrospray ionization source. The 3-phase column was placed ~2 mm from the orifice of the heating capillary. The length of the split column was adjusted to a flow rate between 100-300 nL/min. The three buffer solutions used in this multidimensional capillary HPLC system were 5% ACN/0.1% formic acid (buffer A), 80% ACN/0.1% formic acid (buffer B), and 500 mM ammonium acetate/5% ACN/0.1% formic acid (buffer C). Fully automated 6-cycle chromatography runs were carried out on each sample. The first cycle was a 0-100% buffer B gradient. Each of the following cycles started with a 3 min equilibrium washing with buffer A, a 3-20 min salt wash, followed by a 0-70% buffer B gradient. The isocratic salt concentration increased from 10% to 100% of buffer C. The LCQ was operated via an Instrument Method of Xcaliber. The electrospray voltage was 2.0 kV. The heated capillary was set to 180° C. The capillary voltage was set to 4.5 kV. Each scan was set to acquire a full MS scan between 400 and 1400 m/z followed by three MS/MS scans between 400 and 2000 m/z of the top three intense ions from the preceding MS scan. Relative collision energy for collision-induced dissociation was set to 35%.

IV. Database searching. To increase the size of the M. jannaschii database, the yeast database containing more than 6000 ORF entries was combined with the M. jannaschii database from TIGR, which contains 1775 individual open reading frame (ORF) sequences. A total of 172 contaminant proteins including keratins and proteases were also added into the database. First, all MS/MS spectra were extracted from raw LC/LC/MS/MS data. Then, the algorithm "2 to 3" was used to determine charge states, delete poor-quality MS/MS spectra, and identify MS/MS spectra whose precursor peak has predominant neutral loss of 98 daltons (-H3PO4) (Sadygov and Yates, Anal. Chem. 75, 3792 (2003)). Third, MS/MS spectra after "2 to 3" were searched using Normalized-SEQUEST (MacCoss, et al., Anal. Chem. 74, 5593 (2002)) against the combined database. A molecular mass of 57 daltons was added to the static search of all cysteines to account for carboxyamidomethylation. A molecular mass of 16 daltons was added to differential search of methionine to account for oxidation. DTASelect (Tabb, et al., J. Proteome Res. 1, 21 (2002)) was used to filter, organize and display the searching results. The filter of DTASelect was set at a stringent level to exclude possible false positives. All accepted peptides must have a ΔCn of at least 0.08. All peptides had to be fully or half tryptic. The lowest cross correlation value of the peptides was set to 0.3 (+1, +2, +3 charges). The Sp rank had to be within the top 100 and all proteins had to have at least two peptides passing the above filter criteria. Proteins that are subsets of other proteins were removed. Manual evaluation of the spectrum was also performed for low sequence coverage proteins.

n) Construction of the Integration Vector pIJA03-sepS for M. maripaludis

The integration vector pIJA03 was based on the E. coli plasmid pUC and lacks a suitable replication origin for the methanococci. It contains the pac cassette, which encodes puromycin resistance in methanococci. The pac cassette is flanked by two multiple cloning regions (MCS1 and MCS2) that allows directed cloning of genomic DNA. For construction of pIJA03-sepS vector, 152 bp of the N-terminal end of the sepS gene together with 867 bp of its upstream flanking region were amplified by PCR using M. maripaludis S2 genomic DNA and 5'-AATTGAAACTGCATATGGT-GTCA-TTTACAGGGTGTGT-3' (SEQ ID No. 10) and 5'-CGCGGATCCTCCAAGTGTATCAAATAAAT-3' (SEQ ID No. 11) as primers. The resulting DNA fragment was digested with NdeI and BamHI and inserted into the MCS I of pIJA03 vector at the NdeI and BamHI sites leading to pIJA03-N. The C-terminal end of the *M. maripaludis* S2 sepS gene, 35 bp, together with 1073 bp of its downstream flanking region were amplified by PCR using 5'-CTAGCTAGCATTATCA-AAACAAATTACACTGGAG-3' (SEQ ID No. 12) and 5'-CGGGGTACCCCAGTCTTTTTAAATGTCGA-AG-TAA-3' (SEQ ID No. 13) as primers. The resulting DNA fragment was digested with NheI and KpnI and inserted into the MCS2 of pIJA03-N vector at the NheI and KpnI sites leading to pIJA03-sepS. The orientation and integrity of the fragments were confirmed by DNA sequencing.

o) Media and Culture Conditions of *M. maripaludis*

*M. maripaludis* strain S2 was grown in 28 ml anaerobic culture tubes (Balch tubes) in variations of McN mineral medium as described (W. B. Whitman, J. S. Shieh, S. H. Sohn, D. S. Caras, *Syst. Appl. Microbiol.* 7, 235 (1986)). Variations included the addition of 10 mM sodium acetate and. 1% (v/v) vitamin mixture (McAV), 0.2% (w/v) casamino acids (McCAV) and 0.2% (w/v) yeast extract (McYCAV). 2-Mercaptoethanesulfonic acid (coenzyme M, 3 mM) substituted for cysteine (3 mM) as a reductant, where indicated. An anaerobic 0.5 M stock solution of cysteine (in McAV) was used to add 20 mM cysteine into the medium. This solution was sterilized by filtration.

Replacement of SepS Gene in *Methanococcus maripaludis*

Prior to transformation into *M. maripaludis*, the pIJA03-sepS plasmid was linearized by digestion with PvuI restriction endonuclease. The DNA was transformed into *M. maripaludis* by the polyethylene glycol method (D. L. Tumbula, R. A. Makula, W. B. Whitman, *FEMS Microbiol. Lett.* 121, 309 (1994)). Following transformation, cultures were plated on McYCAV medium +20 mM cysteine +2.5 µM puromycin. Colonies were restreaked on this medium, and well-separated colonies were picked into McYCAV broth +20 mM cysteine +2.5 µM puromycin. Upon growth, early stationary phase cultures were used to prepare frozen stocks. A portion of culture, 1 ml, was centrifuged under anaerobic conditions, and the pellet was resuspended in 1 ml of McCA +30% glycerol. Serum bottles, 2 ml, with red rubber stoppers were used to store the frozen cultures at −70° C.

p) Confirmation of ΔsepS::pac Genotype

Southern hybridizations were performed using the DIG High Prime DNA Labeling and Detection Starter Kit I (Roche, Mannheim, Germany). Genomic DNA was isolated using the Wizard Genomic DNA kit (Promega, Madison, Wis.). The probe was made by double digestion of the pIJA03+sepS plasmid with XhoI and BglII and isolation of the 1.0 kb fragment, which contained the region upstream of the sepS gene. Genomic DNA (3 µg) was digested with EcoRI.

q) Growth Phenotype of ΔsepS::pac Mutant

Prewarmed McAV tubes containing 20 mM cysteine were inoculated from frozen cultures and were incubated at 37° C. until the cultures reached an absorbance (600 nm) of approximately 0.4. The cultures were diluted 1:50 three times for a total culture dilution of 1:125,000, where at time zero the cultures contained approximately 2×10³ cells and less than 0.16 µM of cysteine in the McAV minus cysteine medium. Cultures were grown at 37° C. in a reciprocal shaker and were repressurized 2-3 times per day with 20%CO2:80% H2 gas.

ii. Results and Discussion

Previous investigations of archaeal Cys-tRNA$^{Cys}$ biosynthesis have been hampered by the significant levels of non-cognate tRNA routinely cysteinylated and detected by conventional filter binding assays. This problem was circumvented with a more stringent assay of Cys-tRNA$^{Cys}$ formation: gel-electrophoretic separation of uncharged tRNA from aminoacyl-tRNA (aa-tRNA) and subsequent detection of the tRNA moieties by sequence-specific probing (Varshney et al., *J. Biol. Chem.* 266, 24712 (1991)). Given that *M. jannaschii* is a strict anaerobe, and considering that earlier aerobic purification erroneously identified prolyl-tRNA synthetase (Stathopoulos et al., *Science* 287, 479 (2000) and Lipman, et al., *Biochemistry* 39, 7792 (2000)), anaerobic conditions were used for all procedures unless otherwise indicated. When these procedures were used to monitor acylation of total *M. maripaludis* tRNA by an undialyzed *M. jannaschii* cell-free extract (S-100), tRNA$^{Cys}$ was charged with an amino acid that gave rise to the same mobility shift exhibited by standard *M. maripaludis* Cys-tRNA$^{Cys}$ generated by *M. maripaludis* CysRS (Li et al., *FEBS Lett.* 462, 302 (1999)). Further optimization of the reaction at this stage showed that $Zn^{2+}$ and ATP were also required for the successful formation of charged tRNA$^{Cys}$. When the S-100 fraction was dialyzed, all enzyme activity was lost and could not be recovered by addition of a mixture of the 20 canonical amino acids. These data established that tRNA$^{Cys}$ charging took place in the S-100 extract but not as a result of direct acylation of cysteine to tRNA$^{Cys}$ and not by a Ser-tRNA$^{Cys}$-dependent conversion mechanism (Kim, et al., *J. Bacteriol.* 180, 6446 (1998)). In contrast, the dialyzed S-100 extract supplemented with 20 amino acids formed Ser-tRNA$^{Sec}$, as did *M. maripaludis* seryl-tRNA synthetase. This result is consistent with a tRNA-dependent transformation of serine to selenocysteine (Sec) as seen in bacteria (Böck, et al., in *Aminoacyl-tRNA Synthetases*, Ibba, et al., Eds. (Landes Bioscience, 2004), pp.320-327). On the basis of these results, we reasoned that the Cys-tRNA$^{Cys}$-forming activity consisted of one or more enzymes and some low-molecular-weight substrates that together participated in a tRNA-dependent amino acid biosynthesis pathway.

Figure 2:
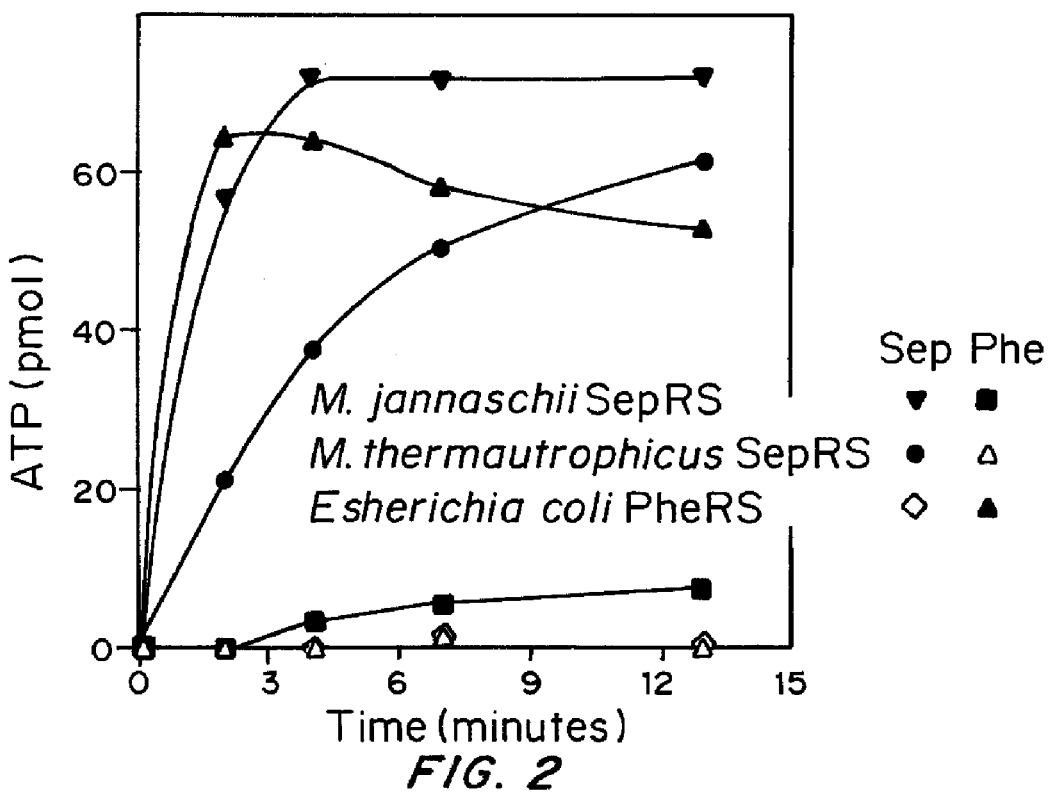
FIG. 2 is a graph of amino acid activation and aminoacylation by SepRS. (A) ATP-inorganic pyrophosphate (PPi) exchange catalyzed by *M. jannaschii* SepRS and Sep or Phe; *M. thermautotrophicus* SepRS and Sep or Phe; and *Escherichia coli* PheRS and Sep or Phe.

To identify the components of the Cys-tRNA$^{Cys}$ biosynthetic pathway, the *M. jannaschii* S-100 extract was separated into two fractions: a low-molecular-mass "filtrate" (Y3) derived by a membrane filtration step (cutoff at 3 kD) and a protein fraction. Addition of Y3 to the dialyzed *M. jannaschii* S-100 restored activity. Both the protein and the filtrate fractions were purified individually by various chromatographic procedures; the activity was assayed by reconstitution of purified fractions from both sources. Chromatographic analysis of the filtrate initially implicated O-phosphoserine (Sep) as one of the components in Y3 necessary for formation of Cys-tRNA$^{Cys}$. This was subsequently verified using the L-enantiomer of this amino acid. Significant advancement in the protein purification strategy was derived from a proteomic analysis of various partially purified column chromatographic fractions (Giometti et al., *J. Chromatogr. B Anal. Technol. Biomed. Life Sci.* 782, 227 (2002)). Repeated liquid chromatography (LC)-mass spectrometry (MS) analysis in the pattern LC-LC-MS-MS identified 20 proteins in the most active fractions, of which 13 were excluded because of their predicted functions or inconsistent phylogenetic distribution. Of the remaining seven proteins, two of the most abundant (Mj1660 and Mj1678) were consistently observed in genomes lacking cysS. Although Mj1660 is a paralog of the α subunit of phenylalanyl-tRNA synthetase (PheRS), it is inactive in Phe-tRNA formation (Das and Vothknecht, *Biochimie* 81, 1037 (1999)). Mj1678 has been annotated as a putative pyridoxal phosphate-dependent enzyme. On the basis of its high homology to known class II aaRSs, it was speculated that Cys-tRNA$^{Cys}$ biosynthesis could be initiated by Mj1660 with Sep as one of the substrates. His$_6$-Mj1660, produced and purified heterologously from *Escherichia coli*, was found to stably attach Sep to tRNACYS in an efficient aerobic ATP-dependent reaction, which suggested that it could function as an aaRS (FIG. 1). However, tRNA$^{Sec}$ was not a substrate for Mj1660. Specificity for Sep was further supported by the observation that His$_6$-Mj1660 and its *M. thermautotrophicus* counterpart His$_6$-Mth1501 both catalyzed Sep-dependent and tRNA-independent ATP-[$^{32}$P]pyrophosphate exchange, a reaction characteristic of aaRSs (FIG. 2) (R. Calendar, P. Berg, *Prog. Nucl. Acid Res. Mol. Biol.* 1, 375 (1966)). No pyrophosphate exchange activity was detected with either His$_6$-Mj1660 or His$_6$-Mth1501 when Sep was replaced by phenylalanine. Sep was unable to stimulate ATP-[32P]pyrophosphate exchange by *E. coli* PheRS, which indicated that it is a specific substrate for Mj1660-type proteins. Analysis of the position of aminoacylation by using *M. thermautotrophicus* total tRNA labeled with [$^{32}$P] in the terminal pA residue showed that Sep was attached to the 3' terminus, the normal site for aminoacylation by aaRSs. A similar conclusion came from the protection against periodate oxidation of charged tRNA$^{Cys}$. In light of these various enzymatic activities and their specificities, we propose that Mj1660-type proteins are classified as aaRSs and are consequently renamed O-phosphoseryl-tRNA synthetase (SepRS, encoded by sepS). Like pyrrolysyl-tRNA synthetase (PylRS), which acylates a suppressor tRNA with pyrrolysine, SepRS belongs to an emerging set of synthetases that use modified amino acids but not their canonical counterparts (Polycarpo et al., *Proc. Natl. Acad. Sci. U.S.A.* 101, 12450 (2004) and Blight et al., *Nature* 431, 333 (2004)). Amino acid sequence similarities indicate that both PylRS and SepRS are subclass IIc aaRSs most closely related to the canonical PheRS. The relative scarcity and narrow phylogenetic distributions of both PylRS and SepRS make it unclear whether these enzymes recently diverged from PheRS or, instead, coevolved with PheRS from a common ancestor.

Figure 3A:
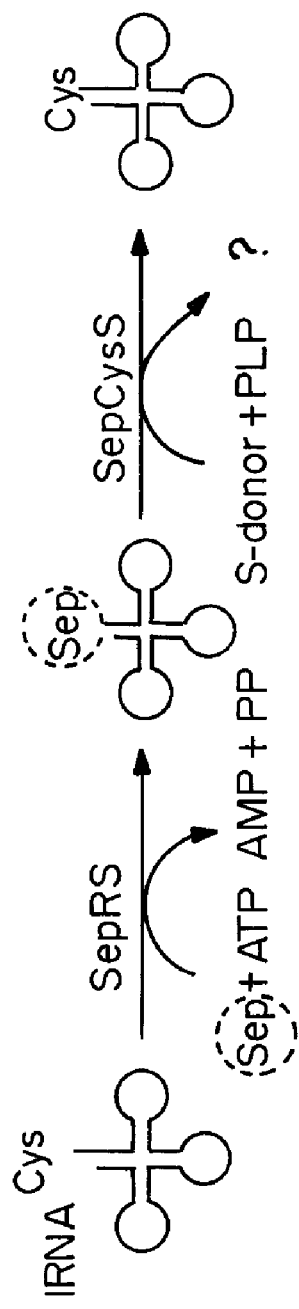
FIG. 3A is a-schematic of Cys-tRNA$^{Cys}$ formation in methanogenic archaea.
Figure 3B:
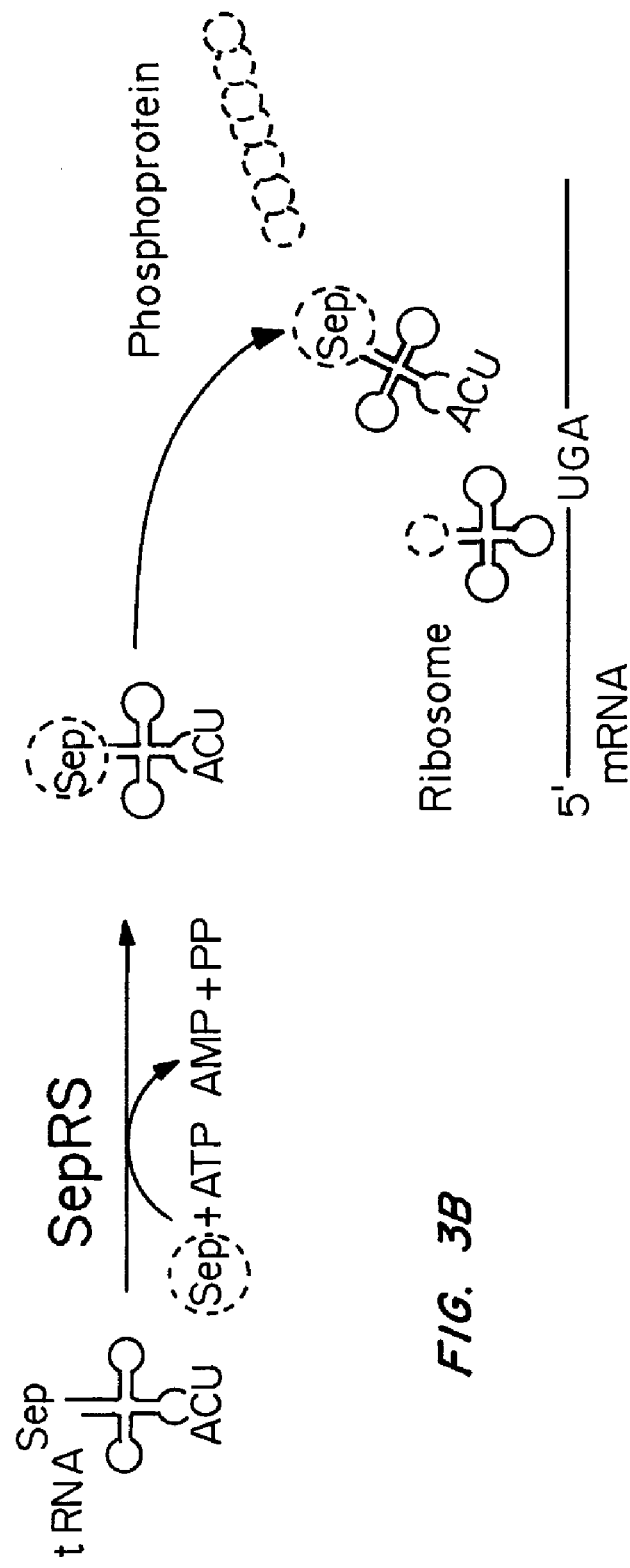
FIG. 3B is a schematic of the targeted incorporation of phosphoserine into peptides or proteins. Phosphoserine (Sep) is cotranslationally incorporated by phosphoserine tRNA synthetase-(SepRS-)mediated charging of tRNASep, a modified tRNA that reads through a UGA stop codon resulting in targeted incorporation of the phosphoserine into a peptide or protein.

Attachment of Sep to tRNA$^{Cys}$ by SepRS is a chemically plausible first step in Cys-tRNA$^{Cys}$ synthesis, as Sep-tRNA could feasibly be converted to Cys-tRNA in the presence of a synthase and the appropriate sulfur donor. Analogous pre-translational amino acid modifications have been described for the synthesis of asparaginyl-, formylmethionyl-, glutaminyl-, and selenocysteinyl-tRNAs (Ibba, et al., *Trends Biochem. Sci.* 25, 311 (2000)). To investigate whether such a transformation accounts for Cys-tRNA$^{Cys}$ formation, preformed Sep-tRNA$^{Cys}$ was incubated with a dialyzed *M. jannaschii* S-100 extract in the presence of Na$_2$S. Electrophoretic analysis of the resulting aa-tRNA indicated formation of a product whose mobility was consistent with Cys-tRNA$^{Cys}$. On the basis of the above proteomic analysis, it was postulated that Mj1678 encoded the enzymatic component responsible for converting Sep-tRNA$^{Cys}$ to Cys-tRNA$^{Cys}$. His$_6$-Mj1678, produced heterologously in *E. coli*, was found to efficiently convert preformed Sep-tRNA$^{Cys}$ into Cys-tRNA$^{Cys}$ in an anaerobic reaction in the presence of pyridoxal phosphate (PLP) and Na$_2$S. The natural sulfur donor of the reaction remains uncharacterized. On the basis of the conversion activity, it appears that Mj1678 is a Sep-tRNA: Cys-tRNA synthase (SepCysS; encoded by pscs). SepRS and SepCysS, both of which are encoded in all archaea lacking cysS, together provide a facile two-step pathway for the synthesis of Cys-tRNA$^{Cys}$ by means of Sep-tRNA$^{Cys}$ (FIG. 3). This route is consistent with the earlier observation that Sep is a precursor of cysteine in *M. jannaschii* (White, *Biochim. Biophys. Acta* 1624, 46 (2003)). As in other organisms (Basurko et al., *IUBMB Life* 48, 525 (1999)), the proposed route of Sep formation involves R-3-phosphoglycerate dehydrogenase (MJ1018) and an phosphoserine aminotransferase.

From available genome sequences, the organismal distributions of SepRS and SepCysS are apparently coupled. To date, sepS and pscS have only been detected in the genomes of the methanogenic archaea *M. jannaschii, M. maripaludis, M. thermautotrophicus, M. kandleri, Methanococcoides burtonii*, the *Methanosarcinaceae*, and in *Arachaeoglobus fulgidus*. Although some of these organisms lack cysS, others, such as *M. maripaludis*, also encode a canonical CysRS and thus contain two potentially functional pathways for Cys-tRNA$^{Cys}$ synthesis (Stathopoulos et al., *Proc. Natl. Acad Sci. U.S.A.* 98, 14292 (2001)). Comparable redundancy is seen for Asn-tRNA$^{Asn}$ synthesis in many bacteria, where the tRNA-dependent route is the sole pathway for asparagine biosynthesis (Min, et al., Proc. Natl. Acad. Sci. USA. 99, 2678 (2002)). Present knowledge of the genes required for archaeal amino acid biosynthesis suggests that the SepRS/SepCysS pathway may provide the only means for de novo production of cysteine in a number of organisms (e.g., *M. jannaschii, M. maripaludis*), whereas other organisms (e.g., *Methanosarcinaceae*) have both tRNA-dependent and tRNA-independent routes to cysteine. In contrast, most nonmethanogenic archaea with known genomes (e.g., *Aeropyrum, Suifolobus, Pyrococcus, Pyrobaculum, Thermoplasma, Picrophilus, Halobacteria*) encode O-acetylserine sulfhydrylase (Mino and Ishikawa, *FEBS Lett.* 551, 133 (2003)) or cysteine synthase, which suggests that cysteine biosynthesis is tRNA-independent in these organisms.

Figure 4:
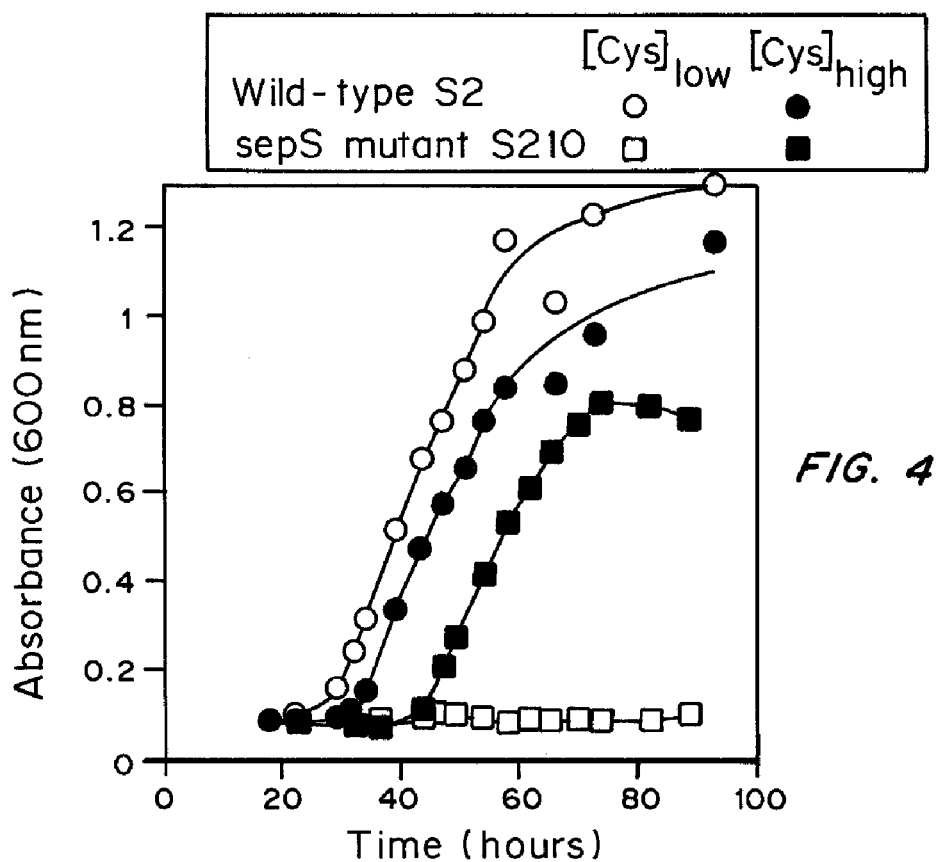
FIG. 4 is a graph of the growth response of the DsepS mutant and wild-type *M. maripaludis* strain S2 to the presence and absence of cysteine in mineral media containing acetate. About 2×10$^3$ cells were inoculated into prewarmed McAV medium containing 3 mM coenzyme M for a final cysteine concentration of <0.16 µM ([Cys]$_{low}$) or into the same medium with 3 mM cysteine ([CYS]$_{high}$). Wild-type S2 (circles), and sepS mutant S210 (squares).
Figure 5:
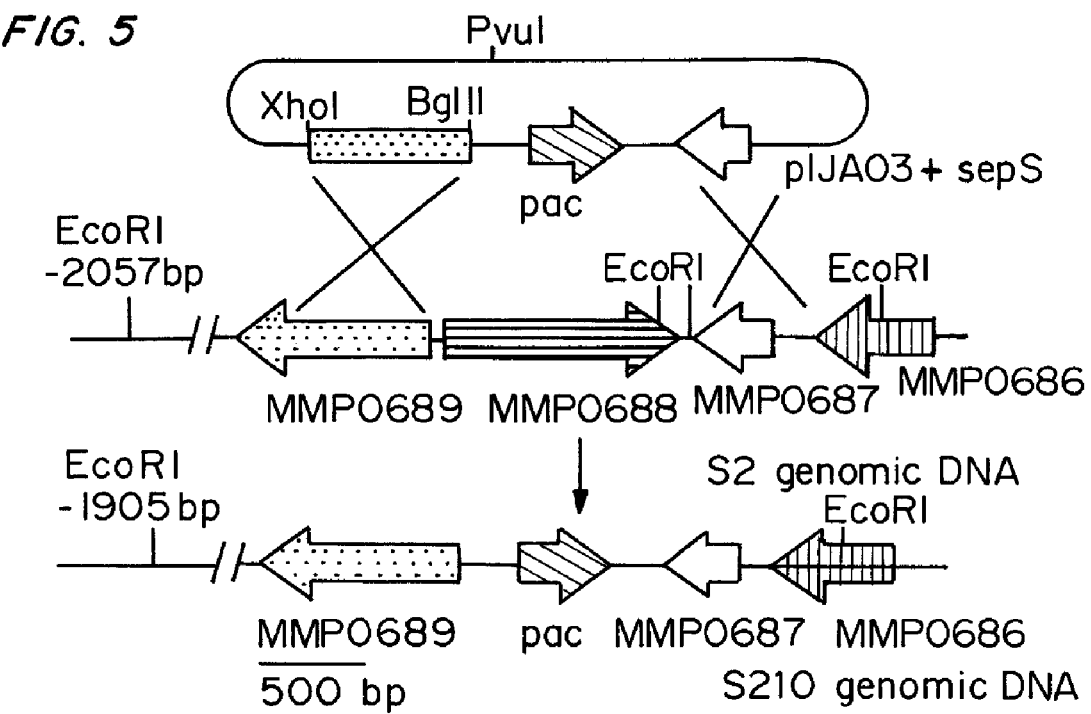
FIG. 5 is a exemplary method for construction of the ΔsepS::pac mutant strain S210. Construction of ΔsepS::pac mutation in *Methanococcus maripaludis* sepS (MMP0688) was performed by transformation of the wild type strain S2 with the suicide vector pIJA03-sepS linearized by PvuI. Upon integration of the plasmid cassette by two homologous recombination events, MMP0688 was replaced with the pac cassette. Other indicated restriction sites were used in Southern hybridization. The EcoRI sites prior to the MMP0689 gene are 2057 and 1905 base pairs (bp) upstream of the sepS or the pac cassette insertion in the S2 and S210 genomes, respectively.

*M. maripaludis*, which has a facile genetic system was used to investigate whether the SepRS/SepCysS pathway can act as the sole route for cysteine biosynthesis. This organism has both a dispensable CysRS (Stathopoulos et al., *Proc. Natl. Acad. Sci. U.S.A.* 98, 14292 (2001)) and the sepS and pscS genes but no known pathway for de novo biosynthesis of free cysteine. Biochemical evidence of a functional SepRS/SepCysS pathway in *M. maripaludis* extracts is described above. In dialyzed extracts of a cysS deletion mutant, Cys-tRNA$^{Cys}$ biosynthesis is dependent on the addition of Sep and Na$_2$S. To test if the SepRS/SepCysS pathway is necessary for cysteine biosynthesis, the sepS gene was deleted from the chromosome of the wild type of *M. maripaludis*. The resulting DsepS strain was a cysteine auxotroph (FIG. 4). Although it grew at a rate comparable to that of wild type on complete medium, it was unable to grow in the absence of exogenous cysteine.

These findings indicate that under certain conditions the SepRS/SepCysS pathway can provide the sole source of cysteine for the cell via Cys-tRNA$^{Cys}$. Reliance on such a route clearly satisfies the requirements for cysteine during protein synthesis, but how cysteine is made available for other metabolic processes is less clear. One possibility is that hydrolysis of Cys-tRNA$^{Cys}$ directly provides free cysteine, as previously proposed for free Asn synthesis via Asn-tRNA$^{Asn}$ in certain bacteria (B. Min, J. T. Pelaschier, D. E. Graham, D. Tumbula-Hansen, D. Söll, *Proc. Natl. Acad. Sci. U.S.A.* 99, 2678 (2002)). In addition, protein turnover in the cell would be expected to contribute more significantly to the cellular cysteine pool when CysRS is absent, as the free amino acid is not itself a substrate for protein synthesis in such cases. Finally, most of the organisms harboring the SepRS/SepCysS pathway are methanogens, which, even in the absence of glutathione, may not require a large pool of free cysteine for redox buffering in the cytoplasm. Methanogens contain high levels of the essential coenzyme 2-mercaptoethanesulfonate (W. E. Balch, R. S. Wolfe, *J. Bacteriol.* 137, 264 (1979)), which may fulfill the redox buffering function of free cysteine. For thermophilic organisms, replacement of the heat-labile cysteine with the thermostable 2-mercaptoethane-sulfonate may be an additional benefit.

These results demonstrate that a class II-type O-phosphoseryl-tRNA synthetase (SepRS) from *Methanocaldococcus jannaschii* acylatess tRNACys with O-phosphoserine (Sep) but not with cysteine. SepRS specifically forms Sep-tRNA-Cys.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

We claim:

1. A method for site specific incorporation of phosphoserine into a protein or polypeptide comprising
    a) providing a nucleic acid sequence encoding a gene with tRNASep activity
    b) providing a nucleic acid sequence encoding a gene with SepRS activity
    c) expressing the nucleic acids of step a) and step b) wherein the SepRS preferentially aminoacylates tRNASep with phosphoserine and the tRNASep recognizes at least one codon such that phosphoserine is incorporated into a protein or polypeptide,
    wherein the nucleic acid sequences encoding genes with tRNASep and SepRS activities are from the genome of *Archaeoglobus fulgidus*, or of a methanogenic archaea selected from the group consisting of *M. jannaschii, M. maripaludis, M. thermautotrophicus, M. kandleri*, or the *Methanosarcinacae*.

2. The method of claim 1 wherein the tRNASep is cysteinyl-tRNA from *Methanocaldococcus jannaschii*.

3. The method of claim 2, wherein the cysteinyl-tRNA is encoded by the nucleic acid sequence of SEQ ID NO:1.

4. The method of claim 1 wherein the SepRS is the class II-type O-phosphoseryl-tRNA synthetase from *Methanocaldococcus jannaschii*.

5. The method of claim 4, wherein the class II-type O-phosphoseryl-tRNA synthetase is encoded by SEQ ID NO:2.

6. The method of claim 1 wherein the nucleic acid encoding a gene with tRNASep activity and the nucleic acid encoding a gene with SepRS activity are on one or more vectors.

7. The method of claim 6 wherein the vector is an expression vector selected from the group consisting of a plasmid, a virus, a naked polynucleotide, and a conjugated polynucleotide.

8. The method of claim 6 wherein the vector is expressed in cells selected from the group consisting of bacterial cells, archeaebacterial cells, and eukaryotic cells.

9. The method of claim 6 wherein the vector is expressed in an in vitro transcription/translation system.

10. The method of claim 9 wherein the vector is transcribed and translated prior to or along with nucleic acids encoding one or more proteins or polypeptides.

11. The method of claim 1 wherein the nucleic acids are expressed in an organism.

12. The method of claim 1 wherein the nucleic acids are under control of a promoter selected from the group consisting of constitutive, inducible and tissue-specific.

13. A kit for producing polypeptides and/or proteins containing phosphoserine comprising a nucleic acid sequence encoding tRNA$^{Sep}$ activity and a nucleic acid sequence encoding SepRS activity,
    wherein the nucleic acid sequences encoding genes with tRNASep and SepRS activities are from the genome of *Archaeoglobus fulgidus*, or of a methanogenic archaea selected from the group consisting of *M. jannaschii, M. maripaludis, M. thermautotrophicus, M. kandleri*, or the *Methanosarcinacae*.

14. The kit of claim 13 wherein the kit further comprises phosphoserine.

15. The kit of claim 14 further comprising a host system for expressing the gene.

\* \* \* \* \*

UNITED STATES PATENT AND TRADEMARK OFFICE
CERTIFICATE OF CORRECTION

| | |
|---|---|
| PATENT NO. | : 7,723,069 B2 |
| APPLICATION NO. | : 11/396439 |
| DATED | : May 25, 2010 |
| INVENTOR(S) | : Dieter Soll and Jesse Rinehart |

It is certified that error appears in the above-identified patent and that said Letters Patent is hereby corrected as shown below:

Title page, Item (75) Inventors, after "Jesse Rinehart, New Haven, CT (US)", please insert --; Anselm Sauerwald, Muenster (DE)--.

Signed and Sealed this
Thirtieth Day of October, 2012

David J. Kappos
*Director of the United States Patent and Trademark Office*